US007129212B2

(12) United States Patent
Narva et al.

(10) Patent No.: US 7,129,212 B2

(45) Date of Patent: Oct. 31, 2006

(54) POLYNUCLEOTIDES, PESTICIDAL PROTEINS, AND NOVEL METHODS OF USING THEM

(75) Inventors: Kenneth E. Narva, Carlsbad, CA (US); Donald J. Merlo, Carmel, IN (US)

(73) Assignee: Mycogen Corporation, Indianapolis, IN (US)

( * ) Notice: Subject to any disclaimer, the term of this patent is extended or adjusted under 35 U.S.C. 154(b) by 446 days.

(21) Appl. No.: 10/698,096

(22) Filed: Oct. 31, 2003

(65) Prior Publication Data

US 2004/0128716 A1 Jul. 1, 2004

Related U.S. Application Data

(63) Continuation-in-part of application No. 09/850,351, filed on May 7, 2001, now Pat. No. 6,656,908, which is a continuation-in-part of application No. 09/307,106, filed on May 7, 1999, now Pat. No. 6,603,063, which is a continuation of application No. 09/073,898, filed on May 6, 1998, now Pat. No. 6,242,669, which is a continuation of application No. 08/960,780, filed on Oct. 30, 1997, now Pat. No. 6,204,435.

(60) Provisional application No. 60/029,848, filed on Oct. 30, 1996.

(51) Int. Cl.
*A61K 38/16* (2006.01)
*C07K 14/32* (2006.01)

(52) U.S. Cl. ........................................ 514/12; 530/350

(58) Field of Classification Search ..................... None
See application file for complete search history.

(56) References Cited

U.S. PATENT DOCUMENTS

| | | | |
|---|---|---|---|
| 4,448,885 | A | 5/1984 | Schnepf et al. |
| 4,467,036 | A | 8/1984 | Schnepf et al. |
| 4,797,276 | A | 1/1989 | Herrnstadt et al. |
| 4,853,331 | A | 8/1989 | Herrnstadt et al. |
| 4,918,006 | A | 4/1990 | Ellar et al. |
| 4,948,734 | A | 8/1990 | Edwards et al. |
| 4,990,332 | A | 2/1991 | Payne et al. |
| 5,039,523 | A | 8/1991 | Payne et al. |
| 5,093,120 | A | 3/1992 | Edwards et al. |
| 5,126,133 | A | 6/1992 | Payne et al. |
| 5,151,363 | A | 9/1992 | Payne |
| 5,164,180 | A | 11/1992 | Payne et al. |
| 5,169,629 | A | 12/1992 | Payne et al. |
| 5,204,237 | A | 4/1993 | Gaertner et al. |
| 5,236,843 | A | 8/1993 | Narva et al. |
| 5,262,399 | A | 11/1993 | Hickle et al. |
| 5,270,448 | A | 12/1993 | Payne |
| 5,281,530 | A | 1/1994 | Sick et al. |
| 5,322,932 | A | 6/1994 | Narva et al. |
| 5,350,577 | A | 9/1994 | Payne |
| 5,426,049 | A | 6/1995 | Sick et al. |
| 5,439,881 | A | 8/1995 | Narva et al. |
| 5,667,993 | A | 9/1997 | Feitelson et al. |
| 5,670,365 | A | 9/1997 | Feitelson |
| 5,770,696 | A | 6/1998 | Warren et al. |
| 5,840,868 | A | 11/1998 | Warren et al. |
| 5,849,870 | A | 12/1998 | Warren et al. |
| 5,866,326 | A | 2/1999 | Warren et al. |
| 5,872,212 | A | 2/1999 | Warren et al. |
| 5,877,012 | A | 3/1999 | Estruch et al. |
| 5,888,801 | A | 3/1999 | Warren et al. |
| 5,889,174 | A | 3/1999 | Warren et al. |

FOREIGN PATENT DOCUMENTS

| | | |
|---|---|---|
| EP | 0 359 472 | 3/1990 |
| WO | WO 94/04684 | 3/1994 |
| WO | WO 94/05771 | 3/1994 |
| WO | WO 94/21795 | 9/1994 |
| WO | WO 94/24264 | 10/1994 |
| WO | WO 96/05314 | 2/1996 |
| WO | WO 96/10083 | 4/1996 |
| WO | WO 98/18932 | 5/1998 |

OTHER PUBLICATIONS

Asano, Shoji et al., "A Unique Activity in *Bacillus thuringiensis* Growth Medium," Appl. Entomol. Zool., 1994, pp. 39-45, vol. 29(1).

Beegle, C.C., "Use of Entomogenous Bacteria in Agroecosystems," Developments in Industrial Microbiology, 1978, pp. 97-104, vol. 20.

Carozzi, N.B. et al., "Prediction of Insecticidal Activity of *Bacillus thuringiensis* Strains by Polymerase . . . ," Appl. & Environ. Microbio., 1991, pp. 3057-3061, vol. 57(11).

Couch, T.L., "Mosquito Pathogenicity of *Bacillus thuringiensis* var. israelensis," Developments in Industrial Microbiology, 1980, pp. 61-76, vol. 22.

Estruch, J.J. et al., "Vip3A, A Novel *Bacillus thuringiensis* Vegetative Insecticidal Protein with a Wide Spectrum . . . ,"Proc. Natl. Acad. Sci. USA, 1996, pp. 5389-5394, vol. 93.

Feitelson, J.S. et al., "*Bacillus thuringiensis*: Insects and Beyond," Bio/Technology, 1992, pp. 271-275, vol. 10.

Gaertner, F.H. and Leo Kim, "Current Applied Recombinant DNA Projects," TIBTECH, 1988, pp. 54-57, vol. 6(4).

Gaertner, F.H., "Cellular Delivery Systems for . . . ," Controlled Delivery of Corp Protection Agents (R.M. Wilkins ed.) 1989, p. 245-255, Taylor and Francis, New York and London.

Gleave, A.P. et al., "Identification of an Insecticidal Crystal Protein from *Bacillus thuringiensis* DSIR517 . . . ," Journal of General Microbiology, 1992, pp. 55-62, vol. 138.

Hofte, H. and H.R. Whiteley, "Insecticidal Crystal Proteins of *Bacillus thurgiensis*," Microbiological Reviews, 1989, pp. 242-255, vol. 53(2).

(Continued)

*Primary Examiner*—Robert A. Wax
(74) *Attorney, Agent, or Firm*—Saliwanchik, Lloyd & Saliwanchik

(57) ABSTRACT

Disclosed and claimed are novel *Bacillus thuringiensis* isolates, pesticidal toxins, and genes. The subject invention also provides novel methods of controlling diamond back moths.

13 Claims, 1 Drawing Sheet

OTHER PUBLICATIONS

Krieg, V.A. et al., "*Bacillus thuringiensis* var. tenevrionis, a new pathotype effective against larvae of Coleoptera," Z. Ang. Ent., 1983, pp. 500-508, vol. 96, Abstract.

Lambert, B. et al., "A *Bacillus thuringiensis* Insecticidal Crystal Protein with a High Activity against Members . . . ," Appl. & Environ. Microbiol., 1996, pp. 80-86, vol. 62(1).

LI, Jade, "Bacterial Toxins," Current Opinion in Structural Biology, 1992, pp. 545-556, vol. 2.

Schnepf, H.E. and H.R. Whiteley, "Cloning and Expression of the *Bacillus thurgiensis* Crystal Protein Gene in . . . ," Proc. Natl. Acad. Sci. USA, 1981, pp. 2893-2897, vol. 78(5).

Shevelev, A.B. et al., "Primary Structure of cryX**, the Novel Delta-endotoxin-related Gene from *Bacillus thuringiensis* spp. galleriae," FEBS, 1993, pp. 79-82, vol. 336(1).

Smulevitch, S.V. et al., "Nucleotide Sequence of a Novel Endotoxin Gene crylg of *Bacillus thuringiensis* ssp. galleriae," FEBS, 1991, pp. 25-28, vol. 293(1-2).

| | | | | | | |
|---|---|---|---|---|---|---|
| **Percent Mortality** | 0 | 0 | 25 | 50 | 75 | 100 |
| **KB59A4-6 Expression** | – | – | + | ++ | +++ | ++++ |
| **Line #** | WT | 34 | 39 | 41 | 20 | 31 |

POLYNUCLEOTIDES, PESTICIDAL PROTEINS, AND NOVEL METHODS OF USING THEM

CROSS-REFERENCE TO RELATED APPLICATIONS

This application is a continuation-in-part of U.S. Ser. No. 09/307,106 (filed May 7, 1999, now U.S. Pat. No. 6,603,063), and a continuation-in-part of U.S. Ser. No. 09/850,351 (filed May 7, 2001, now U.S. Pat. No. 6,656,908), the latter of which is a continuation of application U.S. Ser. No. 08/960,780 (filed Oct. 30, 1997, now U.S. Pat. No. 6,204,435); which claims the benefit of provisional application U.S. Ser. No. 60/029,848 (filed Oct. 30, 1996). U.S. Ser. No. 09/307,106 is also a continuation of application U.S. Ser. No. 09/073,898.

BACKGROUND OF THE INVENTION

Insects and other pests cost farmers billions of dollars annually in crop losses and in the expense of keeping these pests under control. The losses caused by insect pests in agricultural production environments include decrease in crop yield, reduced crop quality, and increased harvesting costs.

The soil microbe *Bacillus thuringiensis* (*B.t.*) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering these *B.t.* endotoxins to agricultural environments are under development, including the use of plants genetically engineered with endotoxin genes for insect resistance and the use of stabilized intact microbial cells as *B.t.* endotoxin delivery vehicles (Gaertner, F. H., L. Kim [1988] *TIBTECH* 6:S4–S7). Thus, isolated *B.t.* endotoxin genes are becoming commercially valuable.

Höfte and Whiteley classified *B.t.* crystal protein genes into four major classes (Höfte, H., H. R. Whiteley [1989] *Microbiological Reviews* 52(2):242–255). The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported (Feitelson, J. S., J. Payne, L. Kim [1992] *Bio/Technology* 10:271–275). CryV has been proposed to designate a class of toxin genes that are nematode-specific. Lambert et al. (Lambert, B., L. Buysse, C. Decock, S. Jansens, C. Piens, B. Saey, J. Seurinck, K. van Audenhove, J. Van Rie, A. Van Vliet, M. Peferoen [1996] *Appl. Environ. Microbiol.* 62(1):80–86) describe the characterization of a Cry9 toxin active against lepidopterans. Published PCT applications WO 94/05771 and WO 94/24264 also describe *B.t.* isolates active against lepidopteran pests. Gleave et al. ([1991] JGM 138:55–62), Shevelev et al. ([1993] FEBS Lett. 336:79–82; and Smulevitch et al. ([1991] FEBS Lett. 293:25–26) also describe *B.t.* toxins. Many other classes of *B.t.* genes have now been identified.

WO 94/21795, WO 96/10083, related U.S. patents, and Estruch, J. J. et al. (1996) PNAS 93:5389–5394 describe toxins obtained from *Bacillus* microbes, wherein the toxins were purportedly produced during vegetative cell growth.

These toxins were thus termed vegetative insecticidal proteins (VIP). These toxins were reported to be distinct from crystal-forming δ-endotoxins. These applications make specific reference to toxins designated Vip1A(a), Vip1A(b), Vip2A(a), Vip2A(b), Vip3A(a), and Vip3A(b). See also Lee et al., *AEM* vol. 69, no. 8 (August 2003), pages 4648–4657, for a discussion of Vip3 mechanism of action and truncation. There are no known reports of Vip3 proteins having activity against diamondback moths (*Plutella xylostella*).

Diamondback moths are known to develop resistance to various chemical pesticides, as well as some *B.t.* Cry toxins such as Cry1Ab, Cry1Ac, and Cry1C. See, e.g., Syed, A. R. (1992), Insecticide resistance in diamondback moth in Malaysia, pp. 437–442, in N. S. Talekar (ed.) *Management of Diamondback Moth and Other Pests: Proceedings of the 2nd International Workshop*, AVRDC, Taiwan; Shelton, A. M., et al. (1993), Resistance of diamondback moth to *Bacillus thuringiensis* subspecies in the field, *J. Econ. Entomol.* 86:697–705; Tabashnik, B. E., et al. (1990), Field development of resistance to *Bacillus thuringiensis* in diamondback moth, *J. Econ. Entomol.* 83:1671–1676; Tabashnik, B. E., et al. (1993), Increasing efficiency of bioassays: evaluating resistance to *Bacillus thuringiensis* in diamondback moth, *J. Econ. Entomol.* 86:635–644; Tanada, H. (1992), Occurrence of resistance to *Bacillus thuringiensis* in diamondback moth, and results of trials for integrated control in a watercress greenhouse, pp. 165–173, in N. S. Talekar (ed.) *Management of Diamondback Moth and Other Crucifer Pests: Proceedings of the 2nd International Workshop*, AVRDC, Taiwan; Zhao, J. Z., et al. (1993), On-farm insecticide resistance monitoring methods for diamondback moth, *Acta Agriculturae Sinica* 1(1):(in press); Zhu, G. R., et al. (1991), Insecticide resistance and management of diamondback moth and imported cabbage worm in P. R. China, *Resistant Pest Management Newsletter* 3(2):25–26; Tabashnik, B. E., (1994), Evolution of resistance to *Bacillus thuringiensis, Annual Review of Entomology* 39:47–49; Metz, T. D., et al. (1995), Transgenic broccoli expressing a *Bacillus thuringiensis* insecticidal crystal protein: Implications for pest resistance management strategies, *Molecular Breeding* 1:309–317; Perez, C. J., et al. (1995), Effect of application technology and *Bacillus thuringiensis* subspecies on management of *B. thuringiensis* subsp. *kurstaki*-resistant diamondback moth (Lepidoptera: Plutellidae), *J. Econ. Entomol.* 88:1113–1119; Shelton, A. M., Jr., et al. (1993), Resistance of diamondback moth (Lepidoptera: Plutellidae) to *Bacillus thuringiensis* subspecies in the field, *J. Econ. Entomol.* 86:697–705; Tang, J. D., et al. (1996), Toxicity of *Bacillus thuringiensis* spore and crystal protein to resistant diamondback moth (*Plutella xylostella*), *Appl. Environ. Microbiol.* 62:564–569; Zhao, J. Z., et al. (2001), Different cross-resistance patterns in the diamondback moth (Lepidoptera: Plutellidae) resistant to *Bacillus thuringiensis* toxin Cry1C, *Journal of Economic Entomology* 94(6):1547–1552; Cao, J., et al. (1999), Transgenic broccoli with high levels of *Bacillus thuringiensis* Cry1C protein control diamondback moth resistant to Cry1A or Cry1C, *Molecular Breeding,* 5(2):131–141.

New classes of toxins and genes are described in WO 98/18932. They are distinct from those disclosed in WO 94/21795, WO 96/10083, WO 98/44137, and Estruch et al.

BRIEF SUMMARY OF THE INVENTION

The subject invention concerns materials and methods useful in the control of non-mammalian pests and, particularly, plant pests. In one embodiment, the subject invention provides novel *B.t.* isolates having advantageous activity against non-mammalian pests. In a further embodiment, the subject invention provides new toxins useful for the control of non-mammalian pests. In a preferred embodiment, these pests are lepidopterans. The toxins of the subject invention are preferably soluble toxins that can be obtained from the supernatant of *Bacillus* cultures.

The subject invention further provides nucleotide sequences that encode toxins of the subject invention. The nucleotide sequences of the subject invention encode toxins that are distinct from previously described toxins. In a specific embodiment, the subject invention provides new toxins having advantageous pesticidal activities.

A preferred class of toxins of the subject invention includes SUP-1 toxins. These toxins, and the genes that encode them, can be characterized in terms of, for example, the size of the toxin or gene, the DNA or amino acid sequence, pesticidal activity, and/or antibody reactivity. In a preferred embodiment, toxins of the subject invention have advantageous and surprising activity against diamond back moths (DBM; *Plutella xylostella*). This is advantageous in part because the subject invention provides a new alternative for controlling DBMs, which are known to develop resistance to some *B.t.* and other pesticides. Thus, the subject invention includes using a toxin of the subject invention in methods of controlling or inhibiting DBMs that have developed resistance ($DBM^R$) to at least one other type of toxin.

The subject invention includes plants cells transformed with at least one polynucleotide sequence of the subject invention such that the transformed plant cells express pesticidal toxins in tissues consumed by target pests. Toxins of the subject invention can be used in combination with other toxins. Transformation of plants with the genetic constructs disclosed herein can be accomplished using techniques well known to those skilled in the art and would typically involve modification of the gene to optimize expression of the toxin in plants. One such preferred sequence is disclosed herein.

BRIEF DESCRIPTION OF THE SEQUENCES

Figure 1:
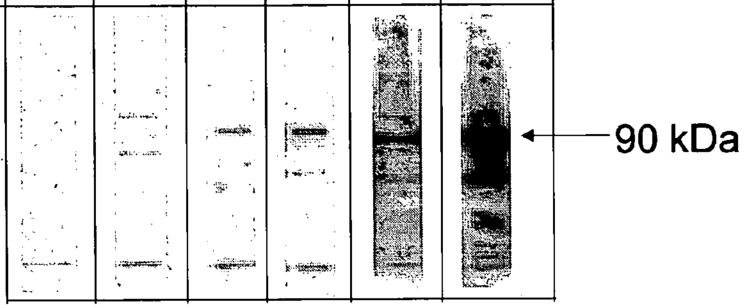
FIG. 1 shows correlation of SEQ ID NO:26 (plant-optimized KB59A4-6) expression and toxicity to tobacco budworm in *Arabidopsis* T1 lines.

SEQ ID NO. 1 is a forward primer, designated "the 339 forward primer," used according to the subject invention.

SEQ ID NO. 2 is a reverse primer, designated "the 339 reverse primer," used according to the subject invention.

SEQ ID NO. 3 is a nucleotide sequence encoding a toxin from *B.t.* strain PS36A.

SEQ ID NO. 4 is an amino acid sequence for the 36A toxin.

SEQ ID NO. 5 is a nucleotide sequence encoding a toxin from *B.t.* strain PS81F.

SEQ ID NO. 6 is an amino acid sequence for the 81F toxin.

SEQ ID NO. 7 is a nucleotide sequence encoding a toxin from *B.t.* strain Javelin 1990.

SEQ ID NO. 8 is an amino acid sequence for the Javelin 1990 toxin.

SEQ ID NO. 9 is a forward primer, designated "158C2 PRIMER A," used according to the subject invention.

SEQ ID NO. 10 is a nucleotide sequence encoding a portion of a soluble toxin from *B.t.* PS158C2.

SEQ ID NO. 11 is a forward primer, designated "49C PRIMER A," used according to the subject invention.

SEQ ID NO. 12 is a nucleotide sequence of a portion of a toxin gene from *B.t.* strain PS49C.

SEQ ID NO. 13 is a forward primer, designated "49C PRIMER B," used according to the subject invention.

SEQ ID NO. 14 is a reverse primer, designated "49C PRIMER C," used according to the subject invention.

SEQ ID NO. 15 is an additional nucleotide sequence of a portion of a toxin gene from PS49C.

SEQ ID NO. 16 is the nucleotide sequence of the SUP toxin gene from *B.t.* strain PS49C.

SEQ ID NO. 17 is the amino acid sequence of the SUP toxin gene from *B.t.* strain PS49C.

SEQ ID NO. 18 is the nucleotide sequence of the SUP toxin gene from *B.t.* strain PS158C2.

SEQ ID NO. 19 is the amino acid sequence of the SUP toxin gene from *B.t.* strain PS158C2.

SEQ ID NO. 20 is a forward primer, designated "SUP-1A," used according to the subject invention.

SEQ ID NO. 21 is a reverse primer, designated "SUP-1B," used according to the subject invention.

SEQ ID NO:22 is a SUP primer for use according to the subject invention.

SEQ ID NO:23 is a SUP primer for use according to the subject invention.

SEQ ID NO:24 is a nucleotide sequence for a SUP gene from KB59A4-6.

SEQ ID NO:25 is an amino acid sequence for a SUP toxin from KB59A4-6.

SEQ ID NO:26 is a plant-optimized polynucleotide that encodes a KB59A4-6 SUP toxin.

SEQ ID NO:27 is a protein encoded by SEQ ID NO:26.

DETAILED DISCLOSURE OF THE INVENTION

The subject invention concerns materials and methods for the control of non-mammalian pests. In specific embodiments, the subject invention pertains to new *Bacillus thuringiensis* isolates and toxins that preferably have activity against lepidopterans. The subject invention further concerns novel genes which encode pesticidal toxins and novel methods for identifying and characterizing *Bacillus* genes which encode toxins with useful properties. The subject invention concerns not only the polynucleotide sequences which encode these toxins, but also the use of these polynucleotide sequences to produce recombinant hosts which express the toxins. The proteins of the subject invention are distinct from protein toxins which have previously been isolated from *Bacillus thuringiensis* (*B.t.*).

*B.t.* isolates useful according to the subject invention have been deposited in the permanent collection of the Agricultural Research Service Patent Culture Collection (NRRL), Northern Regional Research Center, 1815 North University Street; Peoria, Ill. 61604, USA. The culture repository numbers of the *B.t.* strains are as follows:

TABLE 1

| Culture | Repository No. | Deposit Date | Patent No. |
|---|---|---|---|
| B.t. PS11B (MT274) | NRRL B-21556 | Apr. 18, 1996 | |
| B.t. PS31G1 (MT278) | NRRL B-21560 | Apr. 18, 1996 | |
| B.t. PS36A | NRRL B-18929 | Dec. 27, 1991 | |
| B.t. PS49C | NRRL B-21532 | Mar. 14, 1996 | |
| B.t. PS81A2 | NRRL B-18484 | Apr. 19, 1989 | 5,164,180 |
| B.t. PS81F | NRRL B-18424 | Oct. 7, 1988 | 5,045,469 |
| B.t. PS81GG | NRRL B-18425 | Oct. 11, 1988 | 5,169,629 |

TABLE 1-continued

| Culture | Repository No. | Deposit Date | Patent No. |
|---|---|---|---|
| B.t. PS81I | NRRL B-18484 | Apr. 19, 1989 | 5,126,133 |
| B.t. PS85A1 | NRRL B-18426 | Oct. 11, 1988 | |
| B.t. PS86BB1 (MT275) | NRRL B-21557 | Apr. 18, 1996 | |
| B.t. PS86V1 (MT276) | NRRL B-21558 | Apr. 18, 1996 | |
| B.t. PS86W1 (MT277) | NRRL B-21559 | Apr. 18, 1996 | |
| B.t. PS89J3 (MT279) | NRRL B-21561 | Apr. 18, 1996 | |
| B.t. PS91C2 | NRRL B-18931 | Feb. 6, 1991 | |
| B.t. PS158C2 | NRRL B-18872 | Aug. 27, 1991 | 5,268,172 |
| B.t. PS185U2 (MT280) | NRRL B-21562 | Apr. 18, 1996 | |
| B.t. PS192M4 | NRRL B-18932 | Dec. 27, 1991 | 5,273,746 |
| B.t. PS244A2 | NRRL B-21541 | Mar. 14, 1996 | |
| PS94R1 | NRRL B-21801 | Jul. 1, 1997 | |
| PS101DD | NRRL B-21802 | Jul. 1, 1997 | |
| PS202S | NRRL B-21803 | Jul. 1, 1997 | |
| PS213E5 | NRRL B-21804 | Jul. 1, 1997 | |
| PS218G2 | NRRL B-21805 | Jul. 1, 1997 | |

Cultures which have been deposited for the purposes of this patent application were deposited under conditions that assure that access to the cultures is available during the pendency of this patent application to one determined by the Commissioner of Patents and Trademarks to be entitled thereto under 37 CFR 1.14 and 35 U.S.C. 122. The deposits will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the firnishing of a sample of the deposit, and in any case, for a period of at least thirty (30) years after the date of deposit or for the enforceable life of any patent which may issue disclosing the culture(s). The depositor acknowledges the duty to replace the deposit(s) should the depository be unable to furnish a sample when requested, due to the condition of a deposit. All restrictions on the availability to the public of the subject culture deposits will be irrevocably removed upon the granting of a patent disclosing them.

Many of the strains useful according to the subject invention are readily available by virtue of the issuance of patents disclosing these strains or by their deposit in public collections or by their inclusion in commercial products. For example, the *B.t.* strain used in the commercial product, Javelin, is publicly available. The “HD” isolates are publicly available from the Howard Dulmage culture collection.

Mutants of the isolates referred to herein can be made by procedures well known in the art. For example, an asporogenous mutant can be obtained through ethylmethane sulfonate (EMS) mutagenesis of an isolate. The mutants can be made using ultraviolet light and nitrosoguanidine by procedures well known in the art.

In one embodiment, the subject invention concerns materials and methods including nucleotide primers and probes for isolating, characterizing, and identifying *Bacillus* genes encoding protein toxins that are active against non-mammalian pests. The nucleotide sequences described herein can also be used to identify new pesticidal *Bacillus* isolates. The invention further concerns the genes, isolates, and toxins identified using the methods and materials disclosed herein.

The new toxins and polynucleotide sequences provided here are defined according to several parameters. One characteristic of the toxins described herein is pesticidal activity. In a specific embodiment, these toxins have activity against coleopteran and/or lepidopteran pests. The toxins and genes of the subject invention can be further defined by their amino acid and nucleotide sequences. The sequences of the molecules can be defined in terms of homology to certain exemplified sequences as well as in terms of the ability to hybridize with, or be amplified by, certain exemplified probes and primers. The toxins provided herein can also be identified based on their immunoreactivity with certain antibodies.

An important aspect of the subject invention is the identification and characterization of new families of *Bacillus* toxins, and genes which encode these toxins. Members of a preferred family have been designated “SUP” toxins. Toxins within this family, as well as genes encoding toxins within this family, can readily be identified as described herein by, for example, size, amino acid or DNA sequence, and antibody reactivity. Amino acid and DNA sequence characteristics include homology with exemplified sequences, ability to hybridize with DNA probes, and ability to be amplified with specific primers.

SUP toxins of the subject invention are soluble and can be obtained from the supernatant of *Bacillus* cultures as described herein. In a preferred embodiment, the SUP toxins are active against lepidopteran pests. The SUP toxins typically have a size of about 70–100 kDa and, preferably, about 80 kDa. The SUP family is exemplified herein by toxins from isolates PS49C and PS158C2. The subject invention provides probes and primers useful for the identification of toxins and genes in the SUP family These toxins can be used alone or in combination with other toxins to control pestsThese toxins may be used, for example, with δ-endotoxins which are obtained from *Bacillus* isolates.

Table 2 provides a summary of SUP toxins and genes of the subject invention, which can be obtained from particular *B.t.* isolates as shown in Table 2. Genes encoding toxins in each of these families can be identified by a variety of highly specific parameters, including the ability to hybridize with the particular probes set forth in Table 2. Sequence identity in excess of about 80% with the probes set forth in Table 2 can also be used to identify the genes of the various families. Also exemplified are particular primer pairs which can be used to amplify the genes of the subject invention. A portion of a gene within the indicated family would typically be amplifiable with at least one of the enumerated primer pairs. In a preferred embodiment, the amplified portion would be of approximately the indicated fragment size. Primers shown in Table 2 consist of polynucleotide sequences which encode peptides as shown in the sequence listing attached hereto. Additional primers and probes can readily be constructed by those skilled in the art such that alternate polynucleotide sequences encoding the same amino acid sequences can be used to identify and/or characterize additional genes encoding pesticidal toxins. In a preferred embodiment, these additional toxins, and their genes, could be obtained from *Bacillus* isolates.

TABLE 2

| Family | Isolates | Probes (SEQ ID NO.) | Primer Pairs (SEQ ID NOS.) | Fragment size (nt) |
|---|---|---|---|---|
| SUP | PS49C, PS158C2 | 10, 12, 15 | 53 and 54 | 370 |

With the teachings provided herein, one skilled in the art could readily produce and use the various toxins and polynucleotide sequences described herein.

Genes and toxins. The genes and toxins useful according to the subject invention include not only the full length sequences but also fragments of these sequences, variants, mutants, and fusion proteins which retain the characteristic pesticidal activity of the toxins specifically exemplified herein. Chimeric genes and toxins, produced by combining portions from more than one *Bacillus* toxin or gene, may also be utilized according to the teachings of the subject invention. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the exemplified toxins.

It is apparent to a person skilled in this art that genes encoding active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from *Bacillus* isolates and/or DNA libraries using the teachings provided herein. There are a number of methods for obtaining the pesticidal toxins of the instant invention. For example, antibodies to the pesticidal toxins disclosed and claimed herein can be used to identify and isolate toxins from a mixture of proteins. Specifically, antibodies may be raised to the portions of the toxins which are most constant and most distinct from other *Bacillus* toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins are within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying the toxins and genes of the subject invention is through the use of oligonucleotide probes. These probes are detectable nucleotide sequences. Probes provide a rapid method for identifying toxin-encoding genes of the subject invention. The nucleotide segments which are used as probes according to the invention can be synthesized using a DNA synthesizer and standard procedures.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid identity will typically be 60% or greater, preferably 75% or greater, more preferably 80% or greater, more preferably 90% or greater, and can be 95% or greater. These identities are as determined using standard alignment techniques. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 3 provides a listing of examples of amino acids belonging to each class.

TABLE 3

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The δ-endotoxins of the subject invention can also be characterized in terms of the shape and location of toxin inclusions, which are described above.

As used herein, reference to "isolated" polynucleotides and/or "purified" toxins refers to these molecules when they are not associated with the other molecules with which they would be found in nature. Thus, reference to "isolated and purified" signifies the involvement of the "hand of man" as described herein. Chimeric toxins and genes also involve the "hand of man."

As mentioned above, the subject invention includes truncated toxins and chimeric toxins (derived using SEQ ID NOS:17, 19, and 25, for example). As described in U.S. Pat. No. 6,137,033 for example (see also Lee et al. discussed above in the Background section), Vip3 proteins are proteolytically truncated from about 88 kDa to about 66 kDa. The 66 kDa protein comprises amino acid residues 200–789. The 66 kDa protein appears to be further truncated by proteases to yield a 33 kDa toxic core (the C terminus of the 66 kDa protein, corresponding to residues 200–455 of the full-length) and a 45 kDa protein (corresponding to residues 412–789 of the full-length protein).

In light of the diamond back moth (DBM) toxicity exhibited by the 49C and KB59A-46 SUP toxins, very interesting results can be obtained by aligning the sequences of the SUP toxins of the subject invention (SEQ ID NOS:17, 19, and 25, for example) with, for example, those for the proteins of SEQ ID NO:6 (the 81F toxin) and 8, and/or the Vip3 sequences. As can be determined by such alignments (which are within the skill in the art—PLOT SIMILARITY can be used, for example), most of the sequence divergence between 81F vs. 49C and KB59A4-6 occurs in about the last 200 amino acid residues of the protein. This would correspond to about the last two-thirds of the 45 kDa band discussed in the '033 patent.

Thus, it appears that the last 200 or so residues of the SUP proteins, or other regions where there is sequence divergence, could be involved with the mechanism of action accounting for insect specificity. In light of this and other teachings discussed herein and in the art in general, the subject invention includes chimeric toxins comprising certain fragments of the subject SUP toxins. Residues 412 to the C terminus (of SEQ ID NOS: 17, 19, and 25) are preferred for such uses, as are residues ~600 to the C terminus. In other embodiments, residues ~200–455 (of SEQ ID NOS: 17, 19, and 25) can be used for constructing chimerics. Alternatively or in combination with other chimeric approaches, the first 200 or so amino acids of SEQ ID NOS: 17, 19, and 25 can be omitted/removed (in vitro); this would yield truncated toxins or truncated chimeric toxins.

The various segments identified above can be swapped amongst themselves, or they can be used in conjunction with, for example, other sequences disclosed herein or with Vip3 sequences. For example, one of the C terminal segments discussed above (residues 412 to the C terminus of SEQ ID NO:17 and 25, for example [786 and 787, respectively]) can be used with residues 0–412 or 455 of SEQ ID NO:6 (81F) for example. Residues 200–412 or 455 of SEQ ID NO:17 or 25, for example, could be used with the C terminal segment of 81F, for example. Alternatively, Vip3 sequences could be used in place of the 81F segments (together with the 49C or KB59A4-6 segments) discussed above. Thus, if SUP and Vip3 toxins are considered to have three main domains or regions as discussed above, chimerics of the subject invention include those that would comply with the following, where each letter depicts a domain, the subscript number indicates the domains in the order discussed above (N terminal to C terminal), and different letters depict different source SUP or Vip3 proteins: $A_1A_2B_3$, $A_1B_2A_3$, $A_1B_2B_3$, $A_1B_2C_3$, and the like. Preferred embodiments of such chimerics are designed to have toxin activity against diamond back moths. The relative location/sequence/order (1-2-3) of the domains does not necessarily have to be maintained, and it should also be clear that the subject invention includes truncated chimerics, including those where a domain is wholly or partly removed. Examples include $A_2B_3$.

Recombinant hosts. The toxin-encoding genes of the subject invention can be introduced into a wide variety of microbial or plant hosts. Expression of the toxin gene results, directly or indirectly, in the production and maintenance of the pesticide. With suitable microbial hosts, e.g., *Pseudomonas*, the microbes can be applied to the situs of the pest, where they will proliferate and be ingested. The result is a control of the pest. Alternatively, the microbe hosting the toxin gene can be killed and treated under conditions that prolong the activity of the toxin and stabilize the cell. The treated cell, which retains the toxic activity, then can be applied to the environment of the target pest.

A wide variety of ways are available for introducing a *Bacillus* gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Synthetic genes which are functionally equivalent to the toxins of the subject invention can also be used to transform hosts. Methods for the production of synthetic genes can be found in, for example, U.S. Pat. No. 5,380,831.

Treatment of cells. As mentioned above, *Bacillus* or recombinant cells expressing a *Bacillus* toxin can be treated to prolong the toxin activity and stabilize the cell. The pesticide microcapsule that is formed comprises the *Bacillus* toxin within a cellular structure that has been stabilized and will protect the toxin when the microcapsule is applied to the environment of the target pest. Suitable host cells may include either prokaryotes or eukaryotes. As hosts, of particular interest will be the prokaryotes and the lower eukaryotes, such as fungi. The cell will usually be intact and be substantially in the proliferative form when treated, rather than in a spore form.

Treatment of the microbial cell, e.g., a microbe containing the *Bacillus* toxin gene, can be by chemical or physical means, or by a combination of chemical and/or physical means, so long as the technique does not deleteriously affect the properties of the toxin, nor diminish the cellular capability of protecting the toxin. Methods for treatment of microbial cells are disclosed in U.S. Pat. Nos. 4,695,455 and 4,695,462, which are incorporated herein by reference.

Methods and formulations for control of pests. Control of pests using the isolates, toxins, and genes of the subject invention can be accomplished by a variety of methods known to those skilled in the art. These methods include, for example, the application of *Bacillus* isolates to the pests (or their location), the application of recombinant microbes to the pests (or their locations), and the transformation of plants with genes which encode the pesticidal toxins of the subject invention. Transformations can be made by those skilled in the art using standard techniques. Materials necessary for these transformations are disclosed herein or are otherwise readily available to the skilled artisan.

Formulated bait granules containing an attractant and the toxins of the *Bacillus* isolates, or recombinant microbes comprising the genes obtainable from the *Bacillus* isolates disclosed herein, can be applied to the soil. Formulated product can also be applied as a seed-coating or root treatment or total plant treatment at later stages of the crop cycle. Plant and soil treatments of *Bacillus* cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations that contain cells will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Diamondback moths (DBMs) are a particularly troublesome pest in Asia, including Southeast Asia. Thus, the subject invention advantageously includes the transgenic plants and seeds of the subject invention, and the use thereof, in Asia, especially for controlling the development of resistant DBMs.

Polynucleotide probes. It is well known that DNA possesses a fundamental property called base complementarity. In nature, DNA ordinarily exists in the form of pairs of anti-parallel strands, the bases on each strand projecting from that strand toward the opposite strand. The base adenine (A) on one strand will always be opposed to the base thymine (T) on the other strand, and the base guanine (G) will be opposed to the base cytosine (C). The bases are held in apposition by their ability to hydrogen bond in this specific way. Though each individual bond is relatively weak, the net effect of many adjacent hydrogen bonded bases, together with base stacking effects, is a stable joining of the two complementary strands. These bonds can be broken by treatments such as high pH or high temperature, and these conditions result in the dissociation, or "denaturation," of the two strands. If the DNA is then placed in conditions which make hydrogen bonding of the bases thermodynamically favorable, the DNA strands will anneal, or "hybridize," and reform the original double stranded DNA. If carried out under appropriate conditions, this hybridization can be highly specific. That is, only strands with a high degree of base complementarity will be able to form stable double stranded structures. The relationship of the specificity of hybridization to reaction conditions is well known. Thus, hybridization may be used to test whether two pieces of DNA are complementary in their base sequences. It is this hybridization mechanism which facilitates the use of probes of the subject invention to readily detect and characterize DNA sequences of interest.

The probes may be RNA, DNA, or PNA (peptide nucleic acid). The probe will normally have at least about 10 bases, more usually at least about 17 bases, and may have up to about 100 bases or more. Longer probes can readily be utilized, and such probes can be, for example, several kilobases in length. The probe sequence is designed to be at least substantially complementary to a portion of a gene encoding a toxin of interest. The probe need not have perfect complementarity to the sequence to which it hybridizes. The probes may be labelled utilizing techniques which are well known to those skilled in this art.

One approach for the use of the subject invention as probes entails first identifying by Southern blot analysis of a gene bank of the *Bacillus* isolate all DNA segments homologous with the disclosed nucleotide sequences. Thus, it is possible, without the aid of biological analysis, to know in advance the probable activity of many new *Bacillus* isolates, and of the individual gene products expressed by a given *Bacillus* isolate. Such a probe analysis provides a rapid method for identifying potentially commercially valuable insecticidal toxin genes within the multifarious subspecies of *B.t.*

One hybridization procedure useful according to the subject invention typically includes the initial steps of isolating the DNA sample of interest and purifying it chemically. Either lysed bacteria or total fractionated nucleic acid isolated from bacteria can be used. Cells can be treated using known techniques to liberate their DNA (and/or RNA). The DNA sample can be cut into pieces with an appropriate restriction enzyme. The pieces can be separated by size through electrophoresis in a gel, usually agarose or acrylamide. The pieces of interest can be transferred to an immobilizing membrane.

The particular hybridization technique is not essential to the subject invention. As improvements are made in hybridization techniques, they can be readily applied.

The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical. The probe's detectable label provides a means for determining in a known manner whether hybridization has occurred.

In the use of the nucleotide segments as probes, the particular probe is labeled with any suitable label known to those skilled in the art, including radioactive and non-radioactive labels. Typical radioactive labels include $^{32}P$, $^{35}S$, or the like. Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probes may be made inherently fluorescent as described in International Application No. WO 93/16094.

Various degrees of stringency of hybridization can be employed. The more severe the conditions, the greater the complementarity that is required for duplex formation. Severity can be controlled by temperature, probe concentration, probe length, ionic strength, time, and the like. Preferably, hybridization is conducted under moderate to high stringency conditions by techniques well known in the art, as described, for example, in Keller, G. H., M. M. Manak (1987) *DNA Probes*, Stockton Press, New York, N.Y., pp. 169–170.

As used herein "moderate to high stringency" conditions for hybridization refers to conditions which achieve the same, or about the same, degree of specificity of hybridization as the conditions employed by the current applicants. Examples of moderate and high stringency conditions are provided herein. Specifically, hybridization of immobilized DNA on Southern blots with 32P-labeled gene-specific probes was performed by standard methods (Maniatis et al.). In general, hybridization and subsequent washes were carried out under moderate to high stringency conditions that allowed for detection of target sequences with homology to the exemplified toxin genes. For double-stranded DNA gene probes, hybridization was carried out overnight at 20–25° C. below the melting temperature (Tm) of the DNA hybrid in 6×SSPE, 5× Denhardt's solution, 0.1% SDS, 0.1 mg/ml denatured DNA. The melting temperature is described by the following formula (Beltz, G. A., K. A. Jacobs, T. H.

Eickbush, P. T. Cherbas, and F. C. Kafatos [1983] *Methods of Enzymology*, R. Wu, L. Grossman and K. Moldave [eds.] Academic Press, New York 100:266–285).

Tm=81.5° C.+16.6 Log [Na+]+0.41(% G+C)−0.61(% formamide)−600/length of duplex in base pairs.

Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

For oligonucleotide probes, hybridization was carried out overnight at 10–20° C. below the melting temperature (Tm) of the hybrid in 6×SSPE, 5× Denhardt's solution, 0.1% SDS, 0.1 mg/ml denatured DNA. Tm for oligonucleotide probes was determined by the following formula:

Tm (° C.)=2(number T/A base pairs)+4(number G/C base pairs) (Suggs, S. V., T. Miyake, E. H. Kawashime, M. J. Johnson, K. Itakura, and R. B. Wallace [1981] ICN-UCLA *Symp. Dev. Biol. Using Purified Genes*, D. D. Brown [ed.], Academic Press, New York, 23:683–693).

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

Low: 1 or 2×SSPE, room temperature

Low: 1 or 2×SSPE, 42° C.

Moderate: 0.2× or 1×SSPE, 65° C.

High: 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

Thus, mutational, insertional, and deletional variants of the disclosed nucleotide sequences can be readily prepared by methods which are well known to those skilled in the art. These variants can be used in the same manner as the exemplified primer sequences so long as the variants have substantial sequence homology with the original sequence. As used herein, substantial sequence homology refers to homology which is sufficient to enable the variant probe to function in the same capacity as the original probe. Preferably, this homology is greater than 50%; more preferably, this homology is greater than 75%; and most preferably, this homology is greater than 90%. The homology/identity can also be greater than 80%, greater than 85%, or greater than 95%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

PCR technology. Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of β-Globin Genomic Sequences and Restriction Site Analysis for Diagnosis of Sickle Cell Anemia," *Science* 230:1350–1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase which is isolated from the thermophilic bacterium *Thermus aquaticus*, the amplification process can be completely automated. Other enzymes which can be used are known to those skilled in the art.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions and deletions can be produced in a given primer by methods known to an ordinarily skilled artisan.

All of the U.S. patents cited herein are hereby incorporated by reference.

Following are examples which illustrate procedures for practicing the invention. These examples should not be construed as limiting. All percentages are by weight and all solvent mixture proportions are by volume unless otherwise noted.

EXAMPLE 1

Culturing of *Bacillus* Isolates Useful According to the Invention

Growth of cells. The cellular host containing the *Bacillus* insecticidal gene may be grown in any convenient nutrient medium. These cells may then be harvested in accordance with conventional ways. Alternatively, the cells can be treated prior to harvesting.

The *Bacillus* cells of the invention can be cultured using standard art media and fermentation techniques. During the fermentation cycle, the bacteria can be harvested by first separating the *Bacillus* vegetative cells, spores, crystals, and lysed cellular debris from the fermentation broth by means well known in the art. Any *Bacillus* spores or crystal δ-endotoxins formed can be recovered employing well-known techniques and used as a conventional δ-endotoxin *B.t.* preparation. The supernatant from the fermentation process contains toxins of the present invention. The toxins are isolated and purified employing well-known techniques.

A subculture of *Bacillus* isolates, or mutants thereof, can be used to inoculate the following medium, known as TB broth:

| | |
|---|---|
| Tryptone | 12 g/l |
| Yeast Extract | 24 g/l |
| Glycerol | 4 g/l |
| $KH_2PO_4$ | 2.1 g/l |
| $K_2HPO_4$ | 14.7 g/l |
| pH 7.4 | |

The potassium phosphate was added to the autoclaved broth after cooling. Flasks were incubated at 30° C. on a rotary shaker at 250 rpm for 24–36 hours.

The above procedure can be readily scaled up to large fermentors by procedures well known in the art.

The *Bacillus* obtained in the above fermentation, can be isolated by procedures well known in the art. A frequently-used procedure is to subject the harvested fermentation broth to separation techniques, e.g., centrifugation. In a specific embodiment, *Bacillus* proteins useful according the present invention can be obtained from the supernatant. The culture supernatant containing the active protein(s) can be used in bioassays.

Alternatively, a subculture of *Bacillus* isolates, or mutants thereof, can be used to inoculate the following peptone, glucose, salts medium:

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| pH 7.2 | |
| Salts Solution (100 ml) | |
| $MgSO_4$.7H2O | 2.46 g |
| $MnSO_4$.H2O | 0.04 g |
| $ZnSO_4$.7H2O | 0.28 g |
| $FeSO_4$.7H2O | 0.40 g |
| $CaCl_2$ Solution (100 ml) | |
| $CaCl_2.2H_2O$ | 3.66 g |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The *Bacillus* spores and/or crystals, obtained in the above fermentation, can be isolated by procedures well known in the art. A frequently-used procedure is to subject the harvested fermentation broth to separation techniques, e.g., centrifugation.

EXAMPLE 2

Isolation and Preparation of Cellular DNA for PCR

DNA can be prepared from cells grown on Spizizen's agar, or other minimal or enriched agar known to those skilled in the art, for approximately 16 hours. Spizizen's casamino acid agar comprises 23.2 g/l Spizizen's minimal salts [$(NH_4)2SO_4$, 120 g; $K_2HPO_4$, 840 g; $KH_2PO_4$, 360 g; sodium citrate, 60 g; $MgSO_4$ $7H_2O$, 12 g. Total: 1392 g]; 1.0 g/l vitamin-free casamino acids; 15.0 g/l Difco agar. In preparing the agar, the mixture was autoclaved for 30 minutes, then a sterile, 50% glucose solution can be added to a final concentration of 0.5% (1/100 vol). Once the cells are grown for about 16 hours, an approximately 1 $cm^2$ patch of cells can be scraped from the agar into 300 μl of 10 mM Tris-HCl (pH 8.0)–1 mM EDTA. Proteinase K was added to 50 μg/ml and incubated at 55 C for 15 minutes. Other suitable proteases lacking nuclease activity can be used. The samples were then placed in a boiling water bath for 15 minutes to inactivate the proteinase and denature the DNA. This also precipitates unwanted components. The samples are then centrifuged at 14,000×g in an Eppendorf microfuge at room temperature for 5 minutes to remove cellular debris. The supernatants containing crude DNA were transferred to fresh tubes and frozen at 20° C. until used in PCR reactions.

Alternatively, total cellular DNA may be prepared from plate-grown cells using the QIAamp Tissue Kit from Qiagen (Santa Clarita, Calif.) following instructions from the manufacturer.

EXAMPLE 3

Use of PCR Primers to Characterize and/or Identify Toxin Genes

Two primers useful in PCR procedures were designed to identify genes that encode pesticidal toxins. Preferably, these toxins are active against lepidopteran insects. The DNA from 95 *B.t.* strains was subjected to PCR using these primers. Two clearly distinguishable molecular weight bands were visible in "positive" strains, as outlined below. The frequency of strains yielding a 339 bp fragment was 29/95 (31%). This fragment is referred to herein as the "339 bp fragment" even though some small deviation in the exact number of base pairs may be observed.

```
GARCCRTGGA AAGCAAATAA TAARAATGC      (SEQ ID NO. 1)

AAARTTATCT CCCCAWGCTT CATCTCCATT TTG (SEQ ID NO. 2)
```

The strains which were positive for the 339 bp fragment (29 strains) were: PS11B, PS31G1, PS36A, PS49C, PS81A2, PS81F, PS81GG, PS81I, PS85A1, PS86BB1, PS86V1, PS86W1, PS89J3, PS91C2, PS94R1, PS101DD, PS158C2, PS185U2, PS192M4, PS202S, PS213E5, PS218G2, PS244A2, HD29, HD110, HD129, HD525, HD573a, and Javelin 1990.

The 24 strains which gave a larger (approximately 1.2 kb) fragment were: PS24J, PS33F2, PS45B1, PS52A1, PS62B1, PS80PP3, PS86A1, PS86Q3, PS88F16, PS92B, PS101Z2, PS123D1, PS157C1, PS169E, PS177F1, PS177G, PS185L2, PS201L1, PS204C3, PS204G4, PS242H10, PS242K17, PS244A2, PS244D1.

It was found that *Bacillus* strains producing lepidopteran-active proteins yielded only the 339 bp fragment. Few, if any, of the strains amplifying the approximately 1.2 kb fragment had known lepidopteran activity, but rather were coleopteran-, mite-, and/or nematode-active *B.t.* crystal protein producing strains.

EXAMPLE 4

DNA Sequencing of Toxin Genes Producing the 339 Fragment

PCR-amplified segments of toxin genes present in *Bacillus* strains can be readily sequenced. To accomplish this, amplified DNA fragments can be first cloned into the PCR DNA TA-cloning plasmid vector, pCRII, as described by the supplier (Invitrogen, San Diego, Calif.). Individual pCRII clones from the mixture of amplified DNA fragments from each *Bacillus* strain are chosen for sequencing. Colonies are lysed by boiling to release crude plasmid DNA. DNA templates for automated sequencing are amplified by PCR using vector-specific primers flanking the plasmid multiple cloning sites. These DNA templates are sequenced using Applied Biosystems (Foster City, Calif.) automated sequencing methodologies. The polypeptide sequences can be deduced from these nucleotide sequences.

DNA from three of the 29 *B.t.* strains which amplified the 339 bp fragments were sequenced. A DNA sequence encoding a toxin from strain PS36A is shown in SEQ ID NO. 3. An amino acid sequence for the 36A toxin is shown in SEQ ID. NO 4. A DNA sequence encoding a toxin from strain PS81F is shown in SEQ ID NO. 5. An amino acid sequence for the 81F toxin is shown in SEQ ID. NO 6. A DNA sequence encoding a toxin from strain Javelin 1990 is shown in SEQ ID NO. 7. An amino acid sequence for the Javelin 1990 toxin is shown in SEQ ID. NO 8.

EXAMPLE 5

Determination of DNA Sequences from Additional Genes Encoding Toxins from Strains PS158C2 and PS49C Genes encoding novel toxins were identified from isolates PS158C2 and PS49C as follows: Total cellular DNA was extracted from *B.t.* strains using Qiagen (Santa Clarita, Calif.) Genomic-tip 500/G DNA extraction kits according to the supplier and was subjected to PCR using the oligonucleotide primer pairs listed below. Amplified DNA fragments were purified on Qiagen PCR purification columns and were used as templates for sequencing.

For PS158C2, the primers used were as follows.

```
158C2 PRIMER A:
GCTCTAGAAGGAGGTAACTTATGAACAAGAATAATACTAAATTAAGC (SEQ ID NO. 9)

339 reverse:
AAARTTATCT CCCCAWGCTT CATCTCCATT TTG           (SEQ ID NO. 2)
```

The resulting PCR-amplified DNA fragment was approximately 2 kbp in size. This DNA was partially sequenced by dideoxy chain termination using automated DNA sequencing technology (Pekin Elmer/Applied Biosystems, Foster City, Calif.). A DNA sequence encoding a portion of a soluble toxin from PS158C2 is shown in SEQ ID NO. 10.

For PS49C, two separate DNA fragments encoding parts of a novel toxin gene were amplified and sequenced. The first fragment was amplified using the following primer pair:

```
49C PRIMER A:
CATCCTCCCTACACTTTCTAA            (SEQ ID NO. 11)

339 reverse:
AAARTTATCT CCCCAWGCTT CATCTCCATT   (SEQ ID NO. 2)
TTG
```

The resulting approximately 1 kbp DNA fragment was used as a template for automated DNA sequencing. A sequence of a portion of a toxin gene from strain PS49C is shown in SEQ ID NO. 12.

The second fragment was amplified using the following primer pair:

```
49C PRIMER B:
AAATTATGCGCTAAGTCTGC      (SEQ ID NO. 13)

49C PRIMER C:
TTGATCCGGACATAATAAT       (SEQ ID NO. 14)
```

The resulting approximately 0.57 kbp DNA fragment was used as a template for automated DNA sequencing. An additional sequence of a portion of the toxin gene from PS49C is shown in SEQ ID NO. 15.

Full-length sequences of the 49C and 158C2 SUP toxins and genes are provided as SEQ ID NOs:16–19.

EXAMPLE 6

Additional Primers Useful for Characterizing and/or Identifying Toxin Genes

The following primer pair can be used to identify and/or characterize genes of the SUP family:

```
SUP-1A:
GGATTCGTTATCAGAAA         (SEQ ID NO. 20)

SUP-1B:
CTGTYGCTAACAATGTC         (SEQ ID NO. 21)
```

These primers can be used in PCR procedures to amplify a fragment having a predicted size of approximately 370 bp. A band of the predicted size was amplified from strains PS158C2 and PS49C.

EXAMPLE 7

Molecular Cloning and DNA Sequence Analysis of a Novel SUP Toxin Gene from *Bacillus thuringiensis* Strain KB59A4-6

Total cellular DNA was prepared from the *Bacillus thuringensis* strain KB59A4-6 grown to an optical density of 0.5–0.8 at 600 nm visible light in Luria Bertani (LB) broth. DNA was extracted using the Qiagen Genomic-tip 500/G kit and Genomic DNA Buffer Set according to the protocol for Gram positive bacteria (Qiagen Inc.; Valencia, Calif.). DNA was digested with HinDIII and run on 0.7% agarose gels for Southern blot analysis by standard methods (Maniatis et al.). A PCR amplicon containing a Vip3 gene from Javelin-90 genomic DNA was obtained by using the oligos A3A-atg (GCTCTAGAAGGAGGTAACTTATGAACAA-GAATAATACTAAA TTAAGC) (SEQ ID NO. 22) and A3A-taa (GGGGTACCTTACTTAATAGAGACATCG) (SEQ ID NO. 23). This DNA fragment was gel purified and labeled with radioactive $^{32}$P-dCTP using Prime-It II Random Primer Labeling Kit (Stratagene) for use as a probe. Hybridization of Southern blot filters was carried out in a solution of 6×SSPE, 5× Denhardt's solution, 0.1% SDS, 0.1 mg/ml denatured DNA at 42° C. overnight in a shaking water bath. The filters were subsequently washed in 1×SSPE and 0.1% SDS once at 25° C. followed by two additional washes at 37° C. Hybridized filters were then exposed to X-ray film at B80° C. An approximately 1 kbp HinDIII fragment of KB59A4-6 genomic DNA was identified that hybridized to the Javelin 90 SUP probe.

A lambda library of KB59A4-6 genomic DNA was constructed as follows. DNA was partially digested with Sau3A and size-fractionated on agarose gels. The region of the gel containing fragments between 9.0 and 23 kbp was excised and DNA was isolated by electroelution in 0.1×TAE buffer followed by purification over Elutip-d columns (Schleicher and Schuell, Keene, N.H.). Size-fractionated DNA inserts were ligated into BamHI-digested Lambda-Gem 11 (Promega) and recombinant phage were packaged using GigapackIII XL Packing Extract (Stratagene). Phage were plated on *E. coli* VCS257 cells for screening by hybridization. Plaques were transferred to nylon filters and dried under vacuum at 80° C. Hybridization was then performed with the Javelin 90 Sup gene probe as described above. One plaque that gave a positive signal was selected using a Pasteur pipette to obtain a plug. The plug was soaked over-night at room temperature in 1 mL SM buffer+10 uL $CHCl_3$. Large-scale phage DNA preparations (Maniatis et al.) were obtained from liquid lysates of *E. coli* KW251 infected with this phage.

The KB59A4–6 toxin gene was subcloned into the *E. coli/B. thuringiensis* shuttle vector, pHT370 (O. Arantes and D. Lereclus. 1991. Gene 108: 115–119), on an approximately 5.5 kbp SacI/XbaI fragment identified by Southern hybridization. This plasmid subclone was designated pMYC2473. Recombinant *E. coli* XL10-Gold cells (Stratagene) containing this construct are designated MR993. The insecticidal toxin gene was sequenced by primer walking using pMYC2473 plasmid and PCR amplicons as DNA templates. Sequencing reactions were performed using the Dye Terminator Cycle Sequencing Ready Reaction Kit from PE Applied Biosystems and run on a ABI PRISM 377 Automated Sequencer. Sequence data was analyzed using the PE ABI PRISM 377 Collection, Factura, and AutoAssembler software. The DNA sequence and deduced peptide sequence of the KB59A4-6 toxin are reported as new SEQ ID NOs. 24 and 25, respectively.

A subculture of MR993 was deposited in the permanent collection of the Patent Culture Collection (NRRL), Regional Research Center, 1815 North University Street, Peoria, Ill. 61604 USA on May 4, 1999. The accession number is NRRL B-30125.

EXAMPLE 8

Bioassays for Activity Against Lepidopterans and Coleopterans

Biological activity of the toxins and isolates of the subject invention can be confirmed using standard bioassay procedures. One such assay is the budworm-bollworm (*Heliothis virescens* [Fabricius] and *Helicoverpa zea* [Boddie]) assay. Lepidoptera bioassays were conducted with either surface application to artificial insect diet or diet incorporation of samples. All Lepidopteran insects were tested from the neonate stage to the second instar. All assays were conducted with either toasted soy flour artificial diet or black cutworm artificial diet (BioServ, Frenchtown, N.J.).

Diet incorporation can be conducted by mixing the samples with artificial diet at a rate of 6 mL suspension plus 54 mL diet. After vortexing, this mixture is poured into plastic trays with compartmentalized 3-ml wells (Nutrend Container Corporation, Jacksonville, Fla.). A water blank containing no *B.t.* serves as the control. First instar larvae (USDA-ARS, Stoneville, Miss.) are placed onto the diet mixture. Wells are then sealed with Mylar sheeting (ClearLam Packaging, IL) using a tacking iron, and several pinholes are made in each well to provide gas exchange. Larvae were held at 25° C. for 6 days in a 14:10 (light:dark) holding room. Mortality and stunting are recorded after six days.

Bioassay by the top load method utilizes the same sample and diet preparations as listed above. The samples are applied to the surface of the insect diet. In a specific embodiment, surface area ranged from 0.3 to approximately 0.8 $cm^2$ depending on the tray size, 96 well tissue culture plates were used in addition to the format listed above. Following application, samples are allowed to air dry before insect infestation. A water blank containing no *B.t.* can serve as the control. Eggs are applied to each treated well and were then sealed with Mylar sheeting (ClearLam Packaging, IL) using a tacking iron, and pinholes are made in each well to provide gas exchange. Bioassays are held at 25° C. for 7 days in a 14:10 (light:dark) or 28° C. for 4 days in a 14:10 (light:dark) holding room. Mortality and insect stunting are recorded at the end of each bioassay.

Another assay useful according to the subject invention is the Western corn rootworm assay. Samples can be bioassayed against neonate western corn rootworm larvae (*Diabrotica virgifera virgifera*) via top-loading of sample onto an agar-based artificial diet at a rate of 160 ml/$cm^2$. Artificial diet can be dispensed into 0.78 $cm^2$ wells in 48-well tissue culture or similar plates and allowed to harden. After the diet solidifies, samples are dispensed by pipette onto the diet surface. Excess liquid is then evaporated from the surface prior to transferring approximately three neonate larvae per well onto the diet surface by camel's hair brush. To prevent insect escape while allowing gas exchange, wells are heat-sealed with 2-mil punched polyester film with 27HT adhesive (Oliver Products Company, Grand Rapids, Mich.). Bioassays are held in darkness at 25° C., and mortality scored after four days. Analogous bioassays can be performed by those skilled in the art to assess activity against other pests, such as the black cutworm (*Agrotis ipsilon*).

Results are shown in Table 8.

TABLE 8

Genetics and function of concentrated B.t. supernatants screened for lepidopteran and coleopteran activity

| Strain | Approx. 339 bp PCR fragment | Total Protein (μg/cm2) | ca. 80–100 kDa protein (μg/cm2 | H. virescens % mortality | H. virescens Stunting | H. zea % mortality | H. zea Stunting | Diabrotica % mortality |
|---|---|---|---|---|---|---|---|---|
| PS31G1 | + | 8.3 | 2.1 | 70 | yes | 39 | yes | NT |
| PS49C | + | 13.6 | 1.5 | 8 | yes | 8 | no | NT |

TABLE 8-continued

Genetics and function of concentrated B.t. supernatants screened for lepidopteran and coleopteran activity

| Strain | Approx. 339 bp PCR fragment | Total Protein (μg/cm2) | ca. 80–100 kDa protein (μg/cm2 | H. virescens % mortality | H. virescens Stunting | H. zea % mortality | H. zea Stunting | Diabrotica % mortality |
|---|---|---|---|---|---|---|---|---|
| PS81A2 (#1) | + | 30.3 | 2.3 | 100 | yes | 38 | yes | NT |
| PS81A2 (#2) | + | 18.8 | 1.6 | 38 | yes | 13 | no | NT |
| PS81F | ++ | 26 | 5.2 | 100 | yes | 92 | yes | NT |
| PS81I | + | 10.7 | 1.7 | 48 | yes | 13 | no | NT |
| PS185U2 | + | 23.4 | 2.9 | 100 | yes | 100 | yes | NT |
| PS192M4 | + | 10.7 | 2.0 | 9 | no | 4 | yes | NT |
| HD129 | + | 44.4 | 4.9 | 100 | yes | 50 | yes | NT |
| Javelin 1990 | ++ | 43.2 | 3.6 | 100 | yes | 96 | yes | NT |
| water | | | | 0–8 | | 0–4 | | 12 |

*NT = not tested

EXAMPLE 9

Results of Budworm/Bollworm Bioassays

Concentrated liquid supernatant solutions, obtained according to the subject invention, were tested for activity against *Heliothis virescens* (*H.v.*) and *Helicoverpa zea* (*H.z.*). Supernatants from the following isolates were tested and were found to cause mortality against *H.v.*: PS157C1, PS31G1, PS49C, PS81F, PS811, Javelin 1990, PS158C2, PS202S, PS36A, HD110, and HD29. Supernatants from the following isolates were tested are were found to cause significant mortality against *H.z.*: PS31G1, PS49C, PS81F, PS81I, PS157C1, PS158C2, PS36A, HD110, and Javelin 1990.

EXAMPLE 10

Additional Bioassays and Activity Against Diamond Back Moths

The indicated toxin genes were cloned into *E. coli* cells that produced the toxin proteins but were otherwise free of other toxin genes. The following data were obtained using purified toxin protein (obtained from the indicated clones) in standard diet incorporation bioassays. Interestingly, the Vip3-like Jav90 protein was essentially not active against diamond back moths (DBM) while the 49C and KB59A4-6 SUP toxins were active against DBM. (The meaning of the other pest abbreviations used in the tables below are defined in detail in the next example [Example 11].)

TABLE 9

| Strains | Sample Type | CEW | DBM | FAW |
|---|---|---|---|---|
| KB59A4-6-Native | Frozen Extract | 1.2 | 1.4 | 2 |
| 49C-Native | Frozen Extract | 0 | 1.3 | 0 |

TABLE 10

| SUP Clones | Protein Conc. | BAW | BCW | CEW | DBM | FAW | TBW |
|---|---|---|---|---|---|---|---|
| 49C-Native | 20.3 μg/cm$^2$ | 0 | 0 | 0 | 1.6 | 0 | 0 |
| KB59A4-6-Native | 18.75 μg/cm$^2$ | 0 | 0.8 | 0.2 | 1.5 | 1.1 | 0.3 |

TABLE 11

| SUP Clones | Sample # | BAW | BCW | CEW | DBM | FAW | TBW |
|---|---|---|---|---|---|---|---|
| 49C-Native | 77626 | 0 | 0 | 0 | 1.3 | 0 | 0 |
| 49C-Native | 77642 | 0 | 0 | 0 | 1.9 | 0 | 0 |
| KB59A4-6-Native | 77625 | 0 | 0.9 | 0.2 | 1.7 | 1 | 0.7 |

TABLE 12

| SUP Clones | Sample # | Protein Conc | BAW | BCW | CEW | DBM | FAW | TBW |
|---|---|---|---|---|---|---|---|---|
| 49C-Native | 77642 | 243 μg/cm$^2$ | 0 | 0 | 0 | 2 | 0 | 0 |
| KB59A4-6-Native | 77644 | 39.8 μg/cm$^2$ | 0.9 | 1.1 | 1.5 | 2 | 1.9 | 1.1 |

TABLE 13

| Sample | Dose | TBW | CEW | BCW | BAW | FAW | DBM |
|---|---|---|---|---|---|---|---|
| KB59A4-6 N-term tag | 563 μg/cm$^2$ | 1 | 1 | 1 | 1 | 2 | 1.4 |
| KB59A4-6 Native | 91 μg/cm$^2$ | 0.4 | 0.5 | 0.5 | 0.1 | 1 | 1 |
| JAV90 N-term tag | 359 μg/cm$^2$ | 0.8 | 1 | 1 | 1 | 2 | 0 |

TABLE 14

| Sample | Dose (μg/cm$^2$) | TBW | CEW | BCW | FAW | BAW | DBM |
|---|---|---|---|---|---|---|---|
| KB59A4-6 Native | 297 | 0.6 | 1 | 0.3 | 1.3 | 0.3 | 1.6 |
| KB59A4-6 N-term tag | 102 | 0.9 | 0.9 | 0.4 | 1.4 | 0 | 1.6 |
| JAV90 N-term tag | 86 | 0.1 | 0.7 | 0.4 | 0.6 | 1 | 0.3 |

These findings have interesting and important implications, as DBMs are known to develop resistance to Cry1 *B.t.* toxins. Thus, the subject invention includes the use of the subject SUP proteins for controlling (inhibiting) DBMs and for preventing the development of resistant DBMs (including the use of "stacking" a SUP gene with another *B.t.* toxin gene). The subject invention also includes administering said SUP toxin to a resistant DBM, and the use of said toxins in resistance management strategies. See, e.g., Roush, R. T. (1998), Two-toxin strategies for management of insecticidal transgenic crops: Can pyramiding succeed where pesticide mixture have not?, *Philosophical Transactions Royal Society of London* B(353):1777–1786; Ferre, J., et al. (2002), Biochemistry and genetics of insect resistance to *Bacillus thuringiensis, Annual Review of Entomology,* 47:501–533.

EXAMPLE 11

Target Pests

Toxins of the subject invention can be used, alone or in combination with other toxins, to control one or more non-mammalian pests. Some target pests are listed in Table 15. Activity can be confirmed using the bioassays provided herein, adaptations of these bioassays, and/or other bioassays well known to those skilled in the art.

TABLE 15

Target pest species

| ORDER/Common Name | Latin Name |
|---|---|
| LEPIDOPTERA | |
| European Corn Borer | *Ostrinia nubilalis* |
| European Corn Borer resistant to Cry1 (Cry1Ab and/or 1Ac) | *Ostrinia nubilalis* |
| Black Cutworm (BCW) | *Agrotis ipsilon* |
| Fall Armyworm (FAW) | *Spodoptera frugiperda* |
| Southwestern Corn Borer | *Diatraea grandiosella* |
| Corn Earworm/Bollworm (CEW) | *Helicoverpa zea* |
| Tobacco Budworm (TBW) | *Heliothis virescens* |
| Resistant Tobacco Budworm ($TBW^R$) | *Heliothis virescens* |
| Sunflower Head Moth | *Homeosoma ellectellum* |
| Banded Sunflower Moth | *Cochylis hospes* |
| Argentine Looper | *Rachiplusia nu* |
| Spilosoma | *Spilosoma virginica* |
| Bertha Armyworm (BAW) | *Mamestra configurata* |
| Diamondback Moth (DBM) | *Plutella xylostella* |
| Diamondback Moth resistant to a Cry toxin ($DBM^R$) | *Plutella xylostella* |
| COLEOPTERA | |
| Red Sunflower Seed Weevil | *Smicronyx fulvus* |
| Sunflower Stem Weevil | *Cylindrocopturus adspersus* |
| Sunflower Beetle | *Zygoramma exclamationis* |
| Canola Flea Beetle | *Phyllotreta cruciferae* |
| Western Corn Rootworm | *Diabrotica virgifera virgifera* |
| DIPTERA | |
| Hessian Fly | *Mayetiola destructor* |
| HOMOPTERA | |
| Greenbug | *Schizaphis graminum* |
| HEMIPTERA | |
| Lygus Bug | *Lygus lineolaris* |
| NEMATODA | *Heterodera glycines* |

EXAMPLE 17

Plant-Optimized KB59A4-6 Gene

One skilled in the art may produce transgenic plants that produce the protein encoded by an insecticidal protein gene such as described herein. To ensure adequate expression of the insecticidal protein gene in plants, one may design a new coding region that is more suitable for plant expression, yet encodes substantially the same insecticidal protein as the native coding region. Using codon bias tables established for plant genes, one may substitute the codons specifying individual amino acids as are present in the native gene sequence with codons more often found in plant genes. Because the genetic code is redundant for some amino acids, one may choose from amongst one (Met and Trp), two (Phe, Tyr, His, Gln, Asn, Lys, Asp, Glu, and Cys), three (Ile), four (Val, Pro, Thr, Ala, and Gly) or six (Arg, Ser, and Leu) choices to specify an amino acid, depending on the identity of the particular amino acid to be encoded. Accordingly, one can design a plant-optimized DNA sequence that encodes an insecticidal protein as disclosed herein as SEQ ID NO:27; said DNA sequence is set forth as SEQ ID NO:26. It is to be noted that the protein encoded by SEQ ID NO:27 is identical to that of SEQ ID NO:25, except for the addition of an alanine residue as amino acid number two. This additional amino acid is encoded as a consequence of the introduction of the recognition sequence for restriction enzyme Nco I at the ATG translational start codon to facilitate cloning manipulations of the plant-optimized coding region.

To provide appropriate plant gene expression control sequences to the plant-optimized coding region, the DNA fragment containing the coding region was prepared by cutting the DNA of an appropriate clone with restriction enzymes Nco I and Sac I. This coding region-containing DNA fragment was then ligated onto the corresponding ends of an appropriate plasmid cut with Nco I and Sac I, such that a plant promoter derived from the Cassava Vein Mosaic Virus flanked the coding region on the 5' end. Flanking the coding region on the 3' end were the 3' untranslated (UTR) sequences derived from *Agrobacterium tumefaciens* pTi-15955 ORF 24, which specify the termination of transcription and addition of polyadenylate sequences. The entire chimeric gene fragment (containing the promoter, coding region, and 3' UTR) was introduced by Gateway™ recombination (Invitrogen, Carlsbad, Calif.) between the left and right T-DNA borders of a binary vector in preparation for *Agrobacterium tumefaciens*-mediated transformation of *Arabidopsis* plants. Also located between the T-DNA borders of the binary vector, and thus linked to the chimeric gene encoding the insecticidal protein, is a second plant-expressible gene that confers resistance to the herbicide Finale™ to plant cells expressing the gene. By means of this selectable marker gene, it is possible to identify and select for plant cells containing both introduced genes.

Introduction of the chimeric gene encoding the insecticidal protein into *Arabidopsis* cells was accomplished by a floral leaf dip method well known to those skilled in the art. The treated plants were allowed to set seed, and plants derived from transformed seeds (T1 generation) were selected by germinating the seeds in plant growth medium (Sunshine Mix No. 5; SunGro, Vancouver, Canada) and spraying with a solution of a 1:1000 dilution of Finale™ (Aventis Crop Science, Research Triangle Park, NC). Surviving plants were tested for their ability to kill or inhibit the growth of feeding insects.

A typical bioassay for activity against feeding insects utilized cauline leaves placed in the wells of 32-well insect rearing trays containing 1% agar in water, and individual neonate larvae were placed in each well. After 4 days at 28° C., under 16/8 hr light/dark cycles, the numbers of live and dead larvae were determined.

Production of the insecticidal protein by the transformed *Arabidopsis* plants was assayed using an antibody that reacts with the native KB59A4-6 protein. Proteins from 5–10 mg of rosette leaves were extracted by standard procedures, separated by electrophoresis through an 8–16% polyacrylamide gel in running buffer containing 0.1% sodium dodecyl sulfate, and blotted onto nitrocellulose membrane by standard procedures well known to those skilled in the field. The immobilized, insecticidally active proteins present on the membrane were reacted with an antibody solution and their presence was detected by secondary antibody reactivity by standard methods. FIG. 1 summarizes the results of several such assays. Toxicity of the plants to tobacco budworm (*Heliothis virescens*) is seen to correlate well with the level of the 90 kDa insecticidal protein detected in the transformed plants (five T1 lines shown). No antibody-reactive protein is detected in the wild-type (WT) plant protein preparations.

EXAMPLE 18

Insertion of Toxin Genes Into Plants

One aspect of the subject invention is the transformation of plants with genes encoding the insecticidal toxin of the present invention. A preferred "gene" is that of SEQ ID NO:26. The transformed plants are resistant to attack by the target pest.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13 mp series, pACYC184, etc. Accordingly, the sequence encoding the *Bacillus* toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into *Agrobacteria* (Holsters et al. [1978*] Mol. Gen. Genet.* 163:181–187). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives. In biolistic transformation, plasmid DNA or linear DNA can be employed.

The transformed cells are regenerated into morphologically normal plants in the usual manner. If a transformation event involves a germ line cell, then the inserted DNA and corresponding phenotypic trait(s) will be transmitted to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831. Also, advantageously, plants encoding a truncated toxin will be used. The truncated toxin typically will encode about 55% to about 80% of the full length toxin. Methods for creating synthetic *Bacillus* genes for use in plants are known in the art.

It should be understood that the examples and embodiments described herein are for illustrative purposes only and that various modifications or changes in light thereof will be suggested to persons skilled in the art and are to be included within the spirit and purview of this application.

The invention claimed is:

1. An isolated protein that has toxin activity against a lepidopteran pest, wherein said protein comprises SEQ ID No.: 17.

2. A method for controlling a lepidopteran pest wherein said method comprises administering to said pest a protein according to claim 1.

3. The method of claim 2 wherein said lepidopteran pest is a diamond back moth (*Plutella xylostella*).

4. The method of claim 3 wherein said diamond back moth is resistant to another *Bacillus thuringiensis* toxin.

5. The method of claim 3 wherein said protein is produced by and is present in a plant.

6. The method of claim 3 wherein said plant produces another *Bacillus thuringiensis* toxin.

7. The method of claim 5 wherein said plant is selected from the group consisting of cabbage, broccoli, collards, kale, cauliflower, and Brussels sprouts.

8. The method of claim 3 wherein said protein is used as part of a strategy to prevent or control the development of resistant diamond back moths.

9. A truncated or chimeric toxin comprising a segment consisting of residues 200 to the C terminus of SEQ ID No.: 17.

10. The toxin of claim 9 wherein said segment comprises residues 191 to the C terminus of SEQ ID No.: 17.

11. The toxin of claim 9 wherein said segment comprises residues 200 to 412 of SEQ ID No.: 17.

12. The toxin of claim 11 wherein said segment comprises residues 200 to 455 of SEQ ID No.: 17.

13. The chimeric toxin comprising a segment consisting of residues 412 to the C terminus of SEQ ID NO.: 17.

* * * * *

SEQUENCE LISTING

<160> NUMBER OF SEQ ID NOS: 27

<210> SEQ ID NO 1
<211> LENGTH: 29
<212> TYPE: DNA
<213> ORGANISM: Artificial Sequence
<220> FEATURE:
<223> OTHER INFORMATION: 339 forward primer

<400> SEQUENCE: 1
garccrtgga aagcaaataa taaraaatgc 29

<210> SEQ ID NO 2
<211> LENGTH: 33
<212> TYPE: DNA
<213> ORGANISM: Artificial Sequence
<220> FEATURE:
<223> OTHER INFORMATION: 339 reverse primer

<400> SEQUENCE: 2
aaarttatct ccccawgctt catctccatt ttg 33

<210> SEQ ID NO 3
<211> LENGTH: 2375
<212> TYPE: DNA
<213> ORGANISM: Bacillus thuringiensis

<400> SEQUENCE: 3
atgaacaaga ataatactaa attaagcaca agagccttac caagttttat tgattatttt 60
aatggcattt atggatttgc cactggtatc aaagacatta tgaacatgat ttttaaaacg 120
gatacaggtg gtgatctaac cctagacgaa attttaaaga atcagcagtt actaaatgat 180
atttctggta aattggatgg ggtgaatgga agcttaaatg atcttatcgc acagggaaac 240
ttaaatacag aattatctaa ggaaatatta aaaattgcaa atgaacaaaa tcaagtttta 300
aatgatgtta ataacaaact cgatgcgata aatacgatgc ttcgggtata tctacctaaa 360
attacctcta tgttgagtga tgtaatgaaa caaaattatg cgctaagtct gcaaatagaa 420
tacttaagta aacaattgca agagatttct gataagttgg atattattaa tgtaaatgta 480
cttattaact ctacacttac tgaaattaca cctgcgtatc aaaggattaa atatgtgaac 540
gaaaaatttg aggaattaac ttttgctaca gaaactagtt caaaagtaaa aaaggatggc 600
tctcctgcaa atattcttga tgagttaact gagttaactg aactagcgaa aagtgtaaca 660
aaaaatgatg tggatggttt tgaattttac cttaatacat tccacgatgt aatggtagga 720
aataatttat tcgggcgttc agctttaaaa actgcatcgg aattaattac taaagaaaat 780
gtgaaaacaa gtggcagtga ggtcggaaat gtttataact tcttaattgt attaacagct 840
ctgcaagcaa aagcttttct tactttaaca acatgccgaa aattattagg cttagcagat 900
attgattata cttctattat gaatgaacat ttaaataagg aaaaagagga atttagagta 960
aacatcctcc ctacactttc taatactttt tctaatccta attatgcaaa agttaaagga 1020
agtgatgaag atgcaaagat gattgtggaa gctaaaccag gacatgcatt gattgggttt 1080
gaaattagta atgattcaat tacagtatta aaagtatatg aggctaagct aaaacaaaat 1140
tatcaagtcg ataaggattc cttatcggaa gttatttatg gtgatatgga taaattattg 1200
tgcccagatc aatctgaaca aatctattat acaaataaca tagtatttcc aaatgaatat 1260
gtaattacta aaattgattt cactaaaaaa atgaaaactt taagatatga ggtaacagcg 1320

-continued

```
aatttttatg attcttctac aggagaaatt gacttaaata agaaaaaagt agaatcaagt   1380

gaagcggagt ataaaacgtt aagtgctaat gatgatgggg tgtatatgcc gttaggtgtc   1440

atcagtgaaa catttttgac tccgattaat gggtttggcc tccaagctga tgaaaattca   1500

agattaatta ctttaacatg taaatcatat ttaagagaac tactgctagc aacagactta   1560

agcaataaag aaactaaatt gatcgtcccg ccaagtggtt ttattagcaa tattgtagag   1620

aacgggtcca tagaagagga caatttagag ccgtggaaag caaataataa gaatgcgtat   1680

gtagatcata caggcggagt gaatggaact aaagctttat atgttcataa ggacggagga   1740

atttcacaat ttattggaga taatttaaaa ccgaaaactg agtatgtaat ccaatatact   1800

gttaaaggaa aaccttctat tcatttaata gatgaaaata ctggatatat tcattatgaa   1860

gatacaaata ataatttaga agattatcaa actattaata aacgttttac tacaggaact   1920

gatttaaagg gagtgtattt aattttaaaa agtcaaaatg gagatgaagc ttggggagat   1980

aactttatta ttttggaaat tagtccttct gaaaagttat taagtccaga attaattaat   2040

acaaataatt ggacgagtac gggatcaact aatattagcg gtaatacact cactctttat   2100

cagggaggac gagggattct aaaacaaaac cttcaattag atagtttttc aacttataga   2160

gtgtattttt ctgtgtccgg agatgctaat gtaaggatta gaaattctag ggaagtgtta   2220

tttgaaaaaa gatatatgag cggtgctaaa gatgtttctg aaatgttcac tacaaaattt   2280

gagaaagata acttttatat agagctttct caagggaata atttatatgg tggtcctatt   2340

gtacattttt acgatgtctc tattaagtaa cccaa                              2375
```

<210> SEQ ID NO 4
<211> LENGTH: 790
<212> TYPE: PRT
<213> ORGANISM: Bacillus thuringiensis

<400> SEQUENCE: 4

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190
```

-continued

```
Ser Ser Lys Val Lys Lys Asp Gly Ser Pro Ala Asn Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Lys Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Asn Leu Lys Pro Lys
            580                 585                 590

Thr Glu Tyr Val Ile Gln Tyr Thr Val Lys Gly Lys Pro Ser Ile His
        595                 600                 605
```

-continued

```
Leu Ile Asp Glu Asn Thr Gly Tyr Ile His Tyr Glu Asp Thr Asn Asn
    610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Met Phe Thr Thr Lys Phe Glu Lys Asp Asn Phe Tyr Ile Glu
        755                 760                 765

Leu Ser Gln Gly Asn Asn Leu Tyr Gly Gly Pro Ile Val His Phe Tyr
    770                 775                 780

Asp Val Ser Ile Lys Pro
785                 790
```

<210> SEQ ID NO 5
<211> LENGTH: 2370
<212> TYPE: DNA
<213> ORGANISM: Bacillus thuringiensis

<400> SEQUENCE: 5

```
atgaacaaga ataatactaa attaagcaca agagccttac caagttttat tgattatttt     60

aatggcattt atggatttgc cactggtatc aaagacatta tgaacatgat ttttaaaacg    120

gatacaggtg gtgatctaac cctagacgaa attttaaaga atcagcagtt actaaatgat    180

atttctggta aattggatgg ggtgaatgga agcttaaatg atcttatcgc acagggaaac    240

ttaaatacag aattatctaa agaaatatta aaaattgcaa atgaacaaaa tcaagtttta    300

aatgatgttg ataacaaact cgatgcgata aatacgatgc ttcgggtata tctacctaaa    360

attacctcta tgttgagtga tgtaatgaaa caaaattatg cgctaagtct gcaaatagaa    420

tacttaagta aacaattgca agagatttct gataagttgg atattattaa tgtaaatgta    480

cttattaact ctacacttac tgaaattaca cctgcgtatc aaaggattaa atatgtgaac    540

gaaaaatttg aggaattaac ttttgctaca gaaactagtt caaaagtaaa aaaggatggc    600

tctcctgcag atattcttga tgagttaact gagttaactg aactagcgaa aagtgtaaca    660

aaaaatgatg tggatggttt tgaattttac cttaatacat tccacgatgt aatggtagga    720

aataatttat tcgggcgttc agctttaaaa actgcatcgg aattaattac taaagaaaat    780

gtgaaaacaa gtggcagtga ggtcggaaat gtttataact tcttaattgt attaacagct    840

ctgcaagcaa aagcttttct tactttaaca acatgccgaa aattattagg cttagcagat    900

attgattata cttctattat gaatgaacat ttaaataagg aaaaagagga atttagagta    960

aacatcctcc ctacactttc taatactttt tctaatccta attatgcaaa agttaaagga   1020

agtgatgaag atgcaaagat gattgtggaa gctaaaccag gacatgcatt ggttgggttt   1080
```

-continued

```
gaaattagta atgattcaat tacagtatta aaagtatatg aggctaagct aaaacaaaat   1140

tatcaagttg ataaggattc cttatcggaa gttatttatg gtgatatgga taaattattg   1200

tgcccagatc aatctgaaca aatctattat acaaataaca tagtatttcc aaatgaatat   1260

gtaattacta aaattgattt tactaaaaaa atgaaaactt taagatatga ggtaacagcg   1320

aatttttatg attcttctac aggagaaatt gacttaaata agaaaaaagt agaatcaagt   1380

gaagcggagt atagaacgtt aagtgctaat gatgatggag tgtatatgcc gttaggtgtc   1440

atcagtgaaa catttttgac tccgattaat gggtttggcc tccaagctga tgaaaattca   1500

agattaatta ctttaacatg taaatcatat ttaagagaac tactgctagc aacagactta   1560

agcaataaag aaactaaatt gatcgtcccg cccagtggtt ttattaaaaa tattgtagag   1620

aacgggtcca tagaagagga caatttagag ccgtggaaag caaataataa gaatgagtat   1680

gtagatcata caggcggagt gaatggract aaagctttat atgttcataa ggacggagga   1740

atttcacaat ttattggaga taagttaaaa ccgaaaactg agtatgtaat ccaatatact   1800

gttaaaggaa aaccttctat tcatttaaaa gatgaaaata ctggatatat tcattatgaa   1860

gatacaaata ataatttaga agattatcaa actattacta aacgttttac tacaggaact   1920

gatttaaagg gagtgtattt aattttaaaa agtcaaaatg gagatgaagc ttggggagat   1980

aactttatta ttttggaaat tagtccttct gaaaagttat taagtccaga attaattaat   2040

acaaataatt ggacgagtac gggatcaact aatattagcg gtaatacact cactctttat   2100

cagggaggac gaggaattct aaaacaaaac cttcaattag atagtttttc aacttataga   2160

gtgtattttt ctgtgtccgg agatgctaat gtaaggatta gaaattctag ggaagtgtta   2220

tttgaaaaaa gatatatgag cggtgctaaa gatgtttctg aaattttcac tacaaaattt   2280

gggaaagata acttttatat agagctttct caagggaata atttaaatgg tggccctatt   2340

gtacagtttc ccgatgtctc tattaagtaa                                    2370
```

```
<210> SEQ ID NO 6
<211> LENGTH: 789
<212> TYPE: PRT
<213> ORGANISM: Bacillus thuringiensis

<400> SEQUENCE: 6

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asp Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140
```

-continued

```
Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Lys Asn Ile Val Glu Asn Gly Ser Ile
    530                 535                 540

Glu Glu Asp Asn Leu Glu Pro Trp Lys Ala Asn Asn Lys Asn Glu Tyr
545                 550                 555                 560
```

-continued

```
Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Glu Asp Tyr Gln Thr Ile Thr Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Ile Phe Thr Thr Lys Phe Gly Lys Asp Asn Phe Tyr Ile Glu
        755                 760                 765

Leu Ser Gln Gly Asn Asn Leu Asn Gly Gly Pro Ile Val Gln Phe Pro
    770                 775                 780

Asp Val Ser Ile Lys
785


<210> SEQ ID NO 7
<211> LENGTH: 2375
<212> TYPE: DNA
<213> ORGANISM: Bacillus thuringiensis

<400> SEQUENCE: 7

atgaacaaga ataatactaa attaagcaca agagccttac caagttttat tgattatttt      60

aatggcattt atggatttgc cactggtatc aaagacatta tgaacatgat ttttaaaacg     120

gatacaggtg gtgatctaac cctagacgaa attttaaaga atcagcagtt actaaatgat     180

atttctggta aattggatgg ggtgaatgga agcttaaatg atcttatcgc acagggaaac     240

ttaaatacag aattatctaa ggaaatatta aaaattgcaa atgaacaaaa tcaagtttta     300

aatgatgtta ataacaaact cgatgcgata aatacgatgc ttcgggtata tctacctaaa     360

attacctcta tgttgagtga tgtaatgaaa caaaattatg cgctaagtct gcaaatagaa     420

tacttaagta aacaattgca agagatttct gataagttgg atattattaa tgtaaatgta     480

cttattaact ctacacttac tgaaattaca cctgcgtatc aaaggattaa atatgtgaac     540

gaaaaatttg aggaattaac ttttgctaca gaaactagtt caaaagtaaa aaaggatggc     600

tctcctgcag atattcttga tgagttaact gagttaactg aactagcgaa aagtgtaaca     660

aaaaatgatg tggatggttt tgaattttac cttaatacat tccacgatgt aatggtagga     720

aataatttat tcgggcgttc agctttaaaa actgcatcgg aattaattac taaagaaaat     780
```

-continued

```
gtgaaaacaa gtggcagtga ggtcggaaat gtttataact tcttaattgt attaacagct    840

ctgcaagcaa aagcttttct tactttaaca acatgccgaa aattattagg cttagcagat    900

attgattata cttctattat gaatgaacat ttaaataagg aaaaagagga atttagagta    960

aacatcctcc ctacactttc taatactttt tctaatccta attatgcaaa agttaaagga   1020

agtgatgaag atgcaaagat gattgtggaa gctaaaccag gacatgcatt gattgggttt   1080

gaaattagta atgattcaat tacagtatta aaagtatatg aggctaagct aaaacaaaat   1140

tatcaagtcg ataaggattc cttatcggaa gttatttatg gtgatatgga taaattattg   1200

tgcccagatc aatctgaaca aatctattat acaaataaca tagtatttcc aaatgaatat   1260

gtaattacta aaattgattt cactaaaaaa atgaaaactt taagatatga ggtaacagcg   1320

aatttttatg attcttctac aggagaaatt gacttaaata agaaaaaagt agaatcaagt   1380

gaagcggagt atagaacgtt aagtgctaat gatgatgggg tgtatatgcc gttaggtgtc   1440

atcagtgaaa catttttgac tccgattaat gggtttggcc tccaagctga tgaaaattca   1500

agattaatta ctttaacatg taaatcatat ttaagagaac tactgctagc aacagactta   1560

agcaataaag aaactaaatt gatygtcccg ccaagtggtt ttattagcaa tattgtagag   1620

aacgggtcca tagaagagga caatttagag ccgtggaaag caaataataa gaatgcgtat   1680

gtagatcata caggcggagt gaatggaact aaagctttat atgttcataa ggacggagga   1740

atttcacaat ttattggaga taagttaaaa ccgaaaactg agtatgtaat ccaatatact   1800

gttaaaggaa aaccttctat tcatttaaaa gatgaaaata ctggatatat tcattatgaa   1860

gatacaaata ataatttaga agattatcaa actattaata aacgttttac tacaggaact   1920

gatttaaagg gagtgtattt aattttaaaa agtcaaaatg gagatgaagc ttggggagat   1980

aactttatta ttttggaaat tagtccttct gaaaagttat taagtccaga attaattaat   2040

acaaataatt ggacgagtac gggatcaact aatattagcg gtaatacact cactctttat   2100

cagggaggac gagggattct aaaacaaaac cttcaattag atagtttttc aacttataga   2160

gtgtattttt ctgtgtccgg agatgctaat gtaaggatta gaaattctag ggaagtgtta   2220

tttgaaaaaa gatatatgag cggtgctaaa gatgtttctg aaatgttcac tacaaaattt   2280

gagaaagata acttttatat agagctttct caagggaata atttatatgg tggtcctatt   2340

gtacattttt acgatgtctc tattaagtaa cccaa                              2375
```

<210> SEQ ID NO 8
<211> LENGTH: 790
<212> TYPE: PRT
<213> ORGANISM: Bacillus thuringiensis

<400> SEQUENCE: 8

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95
```

-continued

```
Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510
```

-continued

```
Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Met Phe Thr Thr Lys Phe Glu Lys Asp Asn Phe Tyr Ile Glu
        755                 760                 765

Leu Ser Gln Gly Asn Asn Leu Tyr Gly Gly Pro Ile Val His Phe Tyr
    770                 775                 780

Asp Val Ser Ile Lys Pro
785                 790
```

<210> SEQ ID NO 9
<211> LENGTH: 47
<212> TYPE: DNA
<213> ORGANISM: Artificial Sequence
<220> FEATURE:
<223> OTHER INFORMATION: 158C2 Primer A

<400> SEQUENCE: 9
gctctagaag gaggtaactt atgaacaaga ataatactaa attaagc 47

<210> SEQ ID NO 10
<211> LENGTH: 2035
<212> TYPE: DNA
<213> ORGANISM: Bacillus thuringiensis

<400> SEQUENCE: 10
atgaacaaga ataatactaa attaagcgca agggcctacc gagttttatt gattatttta 60
atggcattta tggatttgcc actggtatca aagacattat gaatatgatt tttaaaacgg 120
atacaggtgg taatctaacc ttagacgaaa tcctaaagaa tcagcagtta ctaaatgaga 180

-continued

```
tttctggtaa attggatggg gtaaatggga gcttaaatga tcttatcgca cagggaaact    240

taaatacaga attagctaag caaatcttaa aagttgcaaa tgaacaaaat caagttttaa    300

atgatgttaa taacaaacta gactgcgata aatacgatgc ttaaaatata tctacctaaa    360

attcacatct atgttaagtg atgtactgaa gccaaaatta tgtgcttaag tcttgcaaat    420

tggaattacc tttaagtaac atctgcacct tggcaagaaa tctccgacaa gctagatatt    480

attaacgtaa atgtgcttat taactctacg cttactgaaa ttacacctgc gtatcaacga    540

attaaatatg tgaatgaaaa atttgacgat ttaacttttg ctacagaaaa cactttaaaa    600

gtaaaaaagg atagctctcc tgctgatatt cttgacgagt taactgaatt aactgaacta    660

gcgaaaagtg ttacaaaaaa tgacgtggat ggttttgaat tttaccttaa tacattccat    720

gatgtaatgg tgggaaataa tttattcggt cgttcagctt taaaaactgc ttcggaatta    780

attgctaaag aaaatgtgaa aacaagtggc agtgaagtag gaaatgttta taatttctta    840

attgtattaa cagctctaca agcaaaagct tttcttactt taacaacatg ccgaaaatta    900

ttaggcttag cagatattga ttatacttct atcatgaatg agcatttaaa taaggaaaaa    960

gaggaattta gagtaaacat ccttcccaca ctttctaata ccttttctaa tcctaattat   1020

gcaaaagcta agggaagtaa tgaagataca aagatgattg tggaagctaa accaggatat   1080

gttttggttg gatttgaaat gagcaataat tcaattacag tattaaaagc atatcaagct   1140

aagctaaaaa aagattatca aattgataag gattcgttat cagaaataat atatagtacg   1200

tgatacggat aaattattat gtccggatca atctgaacaa tatattatac aaagaacata   1260

gcatttccaa atgaatatgt tattactaaa attgctttta ctaaaaaaat gaacagttta   1320

aggtatgagg cgacagcgaa tttttatgat tcttctacag gggatattga tctaaataag   1380

acaaaagtag aatcaagtga agcggagtat agtatgctaa aagctagtga tgatgaagtt   1440

tacatgccgc taggtcttat cagtgaaaca tttttaaatc caattaatgg atttaggctt   1500

gcagtcgatg aaaattccag actagtaact ttaacatgta gatcatattt aagagagaca   1560

ttgttagcga cagatttaaa taataaagaa actaaattga ttgtcccacc taatgttttt   1620

attagcaata ttgtagagaa tggaaatata gaaatggaca ccttagaacc atggaaggca   1680

aataatgaga atgcgaatgt agattattca ggcggagtga atggaactag agctttatat   1740

gttcataagg atggtgaatt ctcacatttt attggagaca agttgaaatc taaaacagaa   1800

tacttgattc gatatattgt aaaaggaaaa gcttctattt ttttaaaaga tgaaagaaat   1860

gaaaattaca tttacgagga tacaaataat aatttagaag attatcaaac tattactaaa   1920

cgttttacta caggaactga ttcgacagga ttttatttat tttttactac tcaagatgga   1980

aatgaagctt ggggagacac tttttttctc tagaaagagg taacttatga acaag         2035
```

<210> SEQ ID NO 11
<211> LENGTH: 21
<212> TYPE: DNA
<213> ORGANISM: Artificial Sequence
<220> FEATURE:
<223> OTHER INFORMATION: 49C Primer A

<400> SEQUENCE: 11

```
catcctccct acactttcta a                                                21
```

<210> SEQ ID NO 12
<211> LENGTH: 950
<212> TYPE: DNA
<213> ORGANISM: Bacillus thuringiensis -continued

<400> SEQUENCE: 12
aaactagagg gagtgataag gatgcgaaaa tcattatgga agctaaacct ggatatgctt 60
tagttggatt tgaaataagt aaggattcaa ttgcagtatt aaaagtttat caggcaaagc 120
taaaacacaa ctatcaaatt gataaggatt cgttatcaga aattgtttat ggtgatatag 180
ataaattatt atgtccggat caatctgaac aaatgtatta tacaaataaa atagcatttc 240
caaatgaata tgttatcact aaaattgctt ttactaaaaa actgaacagt ttaagatatg 300
aggtcacagc gaatttttat gactcttcta caggagatat tgatctaaat aagaaaaaaa 360
tagaatcaag tgaagcggag tttagtatgc taaatgctaa taatgatggt gtttatatgc 420
cgataggtac tataagtgaa acatttttga ctccaattaa tggatttggc ctcgtagtcg 480
atgaaaattc aagactagta actttgacat gtaaatcata tttaagagag acattgttag 540
caacagactt aagtaataaa gaaactaaac tgattgtccc acctaatggt tttattagca 600
atattgtaga aaatgggaac ttagagggag aaaacttaga gccgtgggaa agcaaataac 660
aaaaatgcgt atgtagatca taccggaggt gtaaatggaa ctaaagtttt atatgttcat 720
gaggatggtg agttctcaca atttattggg gataaattga aattgaaaac agaatatgta 780
attccatata ttgtaaaggg gaaagctgct atttatttaa aagatgaaaa aaatggggat 840
tacatatcat gaagaaacat cataatgcaa ttgaagattt ttccagctgt aacttcaata 900
atgattttcg catccttatc atccctctag ctttttcata ataggataga 950

<210> SEQ ID NO 13
<211> LENGTH: 20
<212> TYPE: DNA
<213> ORGANISM: Artificial Sequence
<220> FEATURE:
<223> OTHER INFORMATION: 49C Primer B

<400> SEQUENCE: 13
aaattatgcg ctaagtctgc 20

<210> SEQ ID NO 14
<211> LENGTH: 19
<212> TYPE: DNA
<213> ORGANISM: Artificial Sequence
<220> FEATURE:
<223> OTHER INFORMATION: 49C Primer C

<400> SEQUENCE: 14
ttgatccgga cataataat 19

<210> SEQ ID NO 15
<211> LENGTH: 176
<212> TYPE: DNA
<213> ORGANISM: Bacillus thuringiensis

<400> SEQUENCE: 15
gtaaattatg cgctaagtct gcaccttttt tcactgttac taaacatcac ttttcctata 60
tccccttagc tcttatggat tattgagcaa acttatcttg ttaattacta ctccccatca 120
tatgctaaac aaaaaccaaa caaacattat ctattatatg tccggatcaa aatgta 176

<210> SEQ ID NO 16
<211> LENGTH: 2361
<212> TYPE: DNA
<213> ORGANISM: Bacillus thuringiensis -continued

<400> SEQUENCE: 16

```
atgcaaaaaa ataataaatt aagtgtaaag gctttaccaa gtttcattga ttattttaat     60
ggaatttacg gattcgccac tggtatcaaa gatattatga acatgatttt taaaacgaat    120
acaggagggg atctaacctt agacgaaata ttaaaaaatc aacagttact taatgagatt    180
tctggcaaac tggatggagt gaatggcagc ttaaatgatc ttctcgcaca aggaaacttg    240
gatactgaat tatctaagga aatattaaaa attgcaaatg aacagaataa ggttttaaat    300
gatgtaaata caaagcttga tgcgataaat ttaatgctta acacatattt acctaaaatt    360
acttctatgt taagtgatgt aatgaaacaa aattatgcat taggtttgca aatagaatac    420
ctaagcaaac aattaaagga aatttcagat aagctagatg ttattaatgt aaatgtactc    480
attaactcta cacttactga aattacacct gcctatcaaa ggattaaata tgtaaatgaa    540
aaatttgaag cattaacctc tgctacagaa accaatttaa aaacaaaaca agatagctct    600
catacagata ttcttgatga gttaacagag ctaacggaac tagcgaaaag tgtaacaaaa    660
aatgacgtgg atggctttga attttacctt aatacattcc acgatgtaat gattgggaat    720
aatctatttg gacgttcagc tttaaaaaca gcctcggaat taattgcgaa agaaaatttg    780
aaaacaagtg gcagtgaggt aggaaatgtt tataatttct taattgtatt aacagctctg    840
caagcaaaag cttttcttac tttaactaca tgccggaaat tattgggctt agcagatatt    900
gattatactc ctattatgaa tgaacaccta aataaagaaa aagaggaatt tagagtgaac    960
atccttccta cactttctaa tacttttict aatcctaatt atgaaaaagc tagagggagt   1020
gataaggatg cgaaaatcat tatggaagct aaacctggat atgctttagt tggatttgaa   1080
ataagtaagg attcaattgc agtattaaaa gtttatcagg caaagctaaa acacaactat   1140
caaattgata aggattcgtt atcagaaatt gtttatggtg atatagataa attattatgt   1200
ccggatcaat ctgaacaaat gtattataca aataaaatag catttccaaa tgaatatgtt   1260
atcactaaaa ttgcttttac taaaaaactg aacagtttaa gatatgaggt cacagcgaat   1320
ttttatgact cttctacagg agatattgat ctaaataaga aaaaaataga atcaagtgaa   1380
gcggagttta gtatgctaaa tgctaataat gatggtgttt atatgccgat aggtactata   1440
agtgaaacat ttttgactcc aattaatgga tttggcctcg tagtcgatga aaattcaaga   1500
ctagtaactt tgacatgtaa atcatattta agagagacat tgttagcaac agacttaagt   1560
aataaagaaa ctaaactgat tgtcccacct aatggtttta ttagcaatat tgtagaaaat   1620
gggaacttag agggagaaaa cttagagccg tggaaagcaa ataacaaaaa tgcgtatgta   1680
gatcataccg gaggtgtaaa tggaactaaa gttttatatg ttcatgagga tggtgagttc   1740
tcacaattta ttggggataa attgaaattg aaaacagaat atgtaattca atatattgta   1800
aagggaaaag ctgctattta tttaaaagat gaaaaaaatg gggattacat ttatgaagaa   1860
acaaataatg aattagaaga ttttcaagct gttactaaac gttttattac gggaacagat   1920
tcttcaagag ttcatttaat ttttaccagt caaaatggcg aggaagcatt tggaggaaac   1980
tttattattt cagaaattag gccatccgaa gagttattaa gtccagaatt gattaagtcg   2040
gatgcttggg ttggatctca gggaacttgg atctcaggaa attctctcaa tattaatagt   2100
aatgtaaatg gaacctttcg acaaaacctt tcgttagaaa gttattcaac ctatagtatg   2160
aactttaatg tgaatggatt tggcaaggtg acaataagaa attctcgtga agtagtattt   2220
gaaaggagtt atctacagtt ttcctctaaa tatatttcag aaaaattcac aacaacaacc   2280
```

-continued

```
aataatactg ggttatatgt agaactttct cgtgcttcgt ctaggggagt tataaatttc   2340

ggagattttt caatcaagta a                                              2361


<210> SEQ ID NO 17
<211> LENGTH: 786
<212> TYPE: PRT
<213> ORGANISM: Bacillus thuringiensis

<400> SEQUENCE: 17

Met Gln Lys Asn Asn Lys Leu Ser Val Lys Ala Leu Pro Ser Phe Ile
1               5                   10                  15

Asp Tyr Phe Asn Gly Ile Tyr Gly Phe Ala Thr Gly Ile Lys Asp Ile
            20                  25                  30

Met Asn Met Ile Phe Lys Thr Asn Thr Gly Gly Asp Leu Thr Leu Asp
        35                  40                  45

Glu Ile Leu Lys Asn Gln Gln Leu Leu Asn Glu Ile Ser Gly Lys Leu
    50                  55                  60

Asp Gly Val Asn Gly Ser Leu Asn Asp Leu Leu Ala Gln Gly Asn Leu
65                  70                  75                  80

Asp Thr Glu Leu Ser Lys Glu Ile Leu Lys Ile Ala Asn Glu Gln Asn
                85                  90                  95

Lys Val Leu Asn Asp Val Asn Thr Lys Leu Asp Ala Ile Asn Leu Met
            100                 105                 110

Leu Asn Thr Tyr Leu Pro Lys Ile Thr Ser Met Leu Ser Asp Val Met
        115                 120                 125

Lys Gln Asn Tyr Ala Leu Gly Leu Gln Ile Glu Tyr Leu Ser Lys Gln
    130                 135                 140

Leu Lys Glu Ile Ser Asp Lys Leu Asp Val Ile Asn Val Asn Val Leu
145                 150                 155                 160

Ile Asn Ser Thr Leu Thr Glu Ile Thr Pro Ala Tyr Gln Arg Ile Lys
                165                 170                 175

Tyr Val Asn Glu Lys Phe Glu Ala Leu Thr Ser Ala Thr Glu Thr Asn
            180                 185                 190

Leu Lys Thr Lys Gln Asp Ser Ser His Thr Asp Ile Leu Asp Glu Leu
        195                 200                 205

Thr Glu Leu Thr Glu Leu Ala Lys Ser Val Thr Lys Asn Asp Val Asp
    210                 215                 220

Gly Phe Glu Phe Tyr Leu Asn Thr Phe His Asp Val Met Ile Gly Asn
225                 230                 235                 240

Asn Leu Phe Gly Arg Ser Ala Leu Lys Thr Ala Ser Glu Leu Ile Ala
                245                 250                 255

Lys Glu Asn Leu Lys Thr Ser Gly Ser Glu Val Gly Asn Val Tyr Asn
            260                 265                 270

Phe Leu Ile Val Leu Thr Ala Leu Gln Ala Lys Ala Phe Leu Thr Leu
        275                 280                 285

Thr Thr Cys Arg Lys Leu Leu Gly Leu Ala Asp Ile Asp Tyr Thr Pro
    290                 295                 300

Ile Met Asn Glu His Leu Asn Lys Glu Lys Glu Glu Phe Arg Val Asn
305                 310                 315                 320

Ile Leu Pro Thr Leu Ser Asn Thr Phe Ser Asn Pro Asn Tyr Glu Lys
                325                 330                 335

Ala Arg Gly Ser Asp Lys Asp Ala Lys Ile Ile Met Glu Ala Lys Pro
            340                 345                 350
```

-continued

```
Gly Tyr Ala Leu Val Gly Phe Glu Ile Ser Lys Asp Ser Ile Ala Val
        355                 360                 365

Leu Lys Val Tyr Gln Ala Lys Leu Lys His Asn Tyr Gln Ile Asp Lys
    370                 375                 380

Asp Ser Leu Ser Glu Ile Val Tyr Gly Asp Ile Asp Lys Leu Leu Cys
385                 390                 395                 400

Pro Asp Gln Ser Glu Gln Met Tyr Tyr Thr Asn Lys Ile Ala Phe Pro
                405                 410                 415

Asn Glu Tyr Val Ile Thr Lys Ile Ala Phe Thr Lys Lys Leu Asn Ser
            420                 425                 430

Leu Arg Tyr Glu Val Thr Ala Asn Phe Tyr Asp Ser Ser Thr Gly Asp
        435                 440                 445

Ile Asp Leu Asn Lys Lys Lys Ile Glu Ser Ser Glu Ala Glu Phe Ser
    450                 455                 460

Met Leu Asn Ala Asn Asn Asp Gly Val Tyr Met Pro Ile Gly Thr Ile
465                 470                 475                 480

Ser Glu Thr Phe Leu Thr Pro Ile Asn Gly Phe Gly Leu Val Val Asp
                485                 490                 495

Glu Asn Ser Arg Leu Val Thr Leu Thr Cys Lys Ser Tyr Leu Arg Glu
            500                 505                 510

Thr Leu Leu Ala Thr Asp Leu Ser Asn Lys Glu Thr Lys Leu Ile Val
        515                 520                 525

Pro Pro Asn Gly Phe Ile Ser Asn Ile Val Glu Asn Gly Asn Leu Glu
    530                 535                 540

Gly Glu Asn Leu Glu Pro Trp Lys Ala Asn Asn Lys Asn Ala Tyr Val
545                 550                 555                 560

Asp His Thr Gly Gly Val Asn Gly Thr Lys Val Leu Tyr Val His Glu
                565                 570                 575

Asp Gly Glu Phe Ser Gln Phe Ile Gly Asp Lys Leu Lys Leu Lys Thr
            580                 585                 590

Glu Tyr Val Ile Gln Tyr Ile Val Lys Gly Lys Ala Ala Ile Tyr Leu
        595                 600                 605

Lys Asp Glu Lys Asn Gly Asp Tyr Ile Tyr Glu Glu Thr Asn Asn Glu
    610                 615                 620

Leu Glu Asp Phe Gln Ala Val Thr Lys Arg Phe Ile Thr Gly Thr Asp
625                 630                 635                 640

Ser Ser Arg Val His Leu Ile Phe Thr Ser Gln Asn Gly Glu Glu Ala
                645                 650                 655

Phe Gly Gly Asn Phe Ile Ile Ser Glu Ile Arg Pro Ser Glu Glu Leu
            660                 665                 670

Leu Ser Pro Glu Leu Ile Lys Ser Asp Ala Trp Val Gly Ser Gln Gly
        675                 680                 685

Thr Trp Ile Ser Gly Asn Ser Leu Asn Ile Asn Ser Asn Val Asn Gly
    690                 695                 700

Thr Phe Arg Gln Asn Leu Ser Leu Glu Ser Tyr Ser Thr Tyr Ser Met
705                 710                 715                 720

Asn Phe Asn Val Asn Gly Phe Gly Lys Val Thr Ile Arg Asn Ser Arg
                725                 730                 735

Glu Val Val Phe Glu Arg Ser Tyr Leu Gln Phe Ser Ser Lys Tyr Ile
            740                 745                 750

Ser Glu Lys Phe Thr Thr Thr Thr Asn Asn Thr Gly Leu Tyr Val Glu
        755                 760                 765
```

-continued

Leu Ser Arg Ala Ser Ser Arg Gly Val Ile Asn Phe Gly Asp Phe Ser
    770                 775                 780

Ile Lys
785

<210> SEQ ID NO 18
<211> LENGTH: 2361
<212> TYPE: DNA
<213> ORGANISM: Bacillus thuringiensis

<400> SEQUENCE: 18
atgaatatga ataatactaa attaaacgca agggccctac cgagttttat tgattatttt 60
aatggcattt atggatttgc cactggtatc aaagacatta tgaatatgat ttttaaaacg 120
gatacaggtg gtaatctaac cttagacgaa atcctaaaga atcagcagtt actaaatgag 180
atttctggta aattggatgg ggtaaatggg agcttaaatg atcttatcgc acagggaaac 240
ttaaatacag aattagctaa gcaaatctta aaagttgcaa atgaacaaaa tcaagtttta 300
aatgatgtta ataacaaact agatgcgata aattcgatgc ttaaaatata tctacctaaa 360
attacatcta tgttaagtga tgtaatgaag caaaattatg tgctaagctt gcaaatagaa 420
tacttaagta aacaattgca agaaatctcc gacaagctag atattattaa cgtaaatgtg 480
cttattaact ctacgcttac tgaaattaca cctgcgtatc aacgaattaa atatgtgaat 540
gaaaaatttg acgatttaac ttttgctaca gaaaacactt taaaagtaaa aaaggatagc 600
tctcctgctg atattcttga cgagttaact gaattaactg aactagcgaa aagtgttaca 660
aaaaatgacg tggatggttt tgaattttac cttaatacat tccatgatgt aatggtggga 720
aataatttat tcggtcgttc agctttaaaa actgcttcgg aattaattgc taaagaaaat 780
gtgaaaacaa gtggcagtga agtaggaaat gtttataatt tcttaattgt attaacagct 840
ctacaagcaa aagcttttct tactttaaca acatgccgaa aattattagg cttagcagat 900
attgattata cttctatcat gaatgagcat ttaaataagg aaaaagagga atttagagta 960
aacatccttc ccacactttc taataccttt tctaatccta attatgcaaa agctaaggga 1020
agtaatgaag atacaaagat gattgtggaa gctaaaccag gatatgtttt ggttggattt 1080
gaaatgagca ataattcaat tacagtatta aaagcatatc aagctaagct aaaaaaagat 1140
tatcaaattg ataaggattc gttatcagaa ataatatata gtgatacgga taaattatta 1200
tgtccggatc aatctgaaca aatatattat acaaagaaca tagcatttcc aaatgaatat 1260
gttattacta aaattgcttt tactaaaaaa atgaacagtt taaggtatga ggcgacagcg 1320
aatttttatg attcttctac aggggatatt gatctaaata agacaaaagt agaatcaagt 1380
gaagcggagt atagtatgct aaaagctagt gatgatgaag tttacatgcc gctaggtctt 1440
atcagtgaaa catttttaaa tccaattaat ggatttaggc ttgcagtcga tgaaaattcc 1500
agactagtaa ctttaacatg tagatcatat ttaagagaga cattgttagc gacagattta 1560
aataataaag aaactaaatt gattgtccca cctaatgttt ttattagcaa tattgtagag 1620
aatggaaata tagaaatgga caccttagaa ccatggaagg caaataatga gaatgcgaat 1680
gtagattatt caggcggagt gaatggaact agagctttat atgttcataa ggatggtgaa 1740
ttctcacatt ttattggaga caagttgaaa tctaaaacag aatacttgat tcgatatatt 1800
gtaaaaggaa aagcttctat ttttttaaaa gatgaaaaaa atgaaaatta catttacgag 1860
gatacaaata ataatttaga agattatcaa actattacta aacgttttac tacaggaact 1920
gattcgacag gagtttattt aatttttaat agtcaaaatg gagatgaagc ttggggagat 1980

-continued

```
aactttatta ttttggaaat tagtccgtgt gaaaagttat taagtccaga attaattaaa   2040

acagataaat ggattagtac gggatcgact tatattagcg atgatagact cactctttat   2100

cagggaggac gaggaatttt aaagcaaaac cttcaattag atcgtttttc aacttataga   2160

gtcaattttt ctgtgaacgg agatgctaat gtaaggattc gtaattctag ggaagtgtta   2220

cttgaaaaaa gatatttgaa ccgtaaaggt gtttctgaaa tgttcactac aaaatttgat   2280

aaagataact tttatgtaga gctttctcaa ggggataatc ttggtactgt tgtacatttt   2340

tatgatttct ctattaaata a                                             2361


<210> SEQ ID NO 19
<211> LENGTH: 786
<212> TYPE: PRT
<213> ORGANISM: Bacillus thuringiensis

<400> SEQUENCE: 19

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ala Lys Gln Ile Leu Lys Val Ala Asn Glu Gln
                85                  90                  95

Asn Gln Val Leu Asn Asp Val Asn Asn Lys Leu Asp Ala Ile Asn Ser
            100                 105                 110

Met Leu Lys Ile Tyr Leu Pro Lys Ile Thr Ser Met Leu Ser Asp Val
        115                 120                 125

Met Lys Gln Asn Tyr Val Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Asp Asp Leu Thr Phe Ala Thr Glu Asn
            180                 185                 190

Thr Leu Lys Val Lys Lys Asp Ser Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300
```

-continued

```
Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Ala Lys Gly Ser Asn Glu Asp Thr Lys Met Ile Val Glu Ala Lys
            340                 345                 350

Pro Gly Tyr Val Leu Val Gly Phe Glu Met Ser Asn Asn Ser Ile Thr
        355                 360                 365

Val Leu Lys Ala Tyr Gln Ala Lys Leu Lys Lys Asp Tyr Gln Ile Asp
    370                 375                 380

Lys Asp Ser Leu Ser Glu Ile Ile Tyr Ser Asp Thr Asp Lys Leu Leu
385                 390                 395                 400

Cys Pro Asp Gln Ser Glu Gln Ile Tyr Tyr Thr Lys Asn Ile Ala Phe
                405                 410                 415

Pro Asn Glu Tyr Val Ile Thr Lys Ile Ala Phe Thr Lys Lys Met Asn
            420                 425                 430

Ser Leu Arg Tyr Glu Ala Thr Ala Asn Phe Tyr Asp Ser Ser Thr Gly
        435                 440                 445

Asp Ile Asp Leu Asn Lys Thr Lys Val Glu Ser Ser Glu Ala Glu Tyr
    450                 455                 460

Ser Met Leu Lys Ala Ser Asp Asp Glu Val Tyr Met Pro Leu Gly Leu
465                 470                 475                 480

Ile Ser Glu Thr Phe Leu Asn Pro Ile Asn Gly Phe Arg Leu Ala Val
                485                 490                 495

Asp Glu Asn Ser Arg Leu Val Thr Leu Thr Cys Arg Ser Tyr Leu Arg
            500                 505                 510

Glu Thr Leu Leu Ala Thr Asp Leu Asn Asn Lys Glu Thr Lys Leu Ile
        515                 520                 525

Val Pro Pro Asn Val Phe Ile Ser Asn Ile Val Glu Asn Gly Asn Ile
    530                 535                 540

Glu Met Asp Thr Leu Glu Pro Trp Lys Ala Asn Asn Glu Asn Ala Asn
545                 550                 555                 560

Val Asp Tyr Ser Gly Gly Val Asn Gly Thr Arg Ala Leu Tyr Val His
                565                 570                 575

Lys Asp Gly Glu Phe Ser His Phe Ile Gly Asp Lys Leu Lys Ser Lys
            580                 585                 590

Thr Glu Tyr Leu Ile Arg Tyr Ile Val Lys Gly Lys Ala Ser Ile Phe
        595                 600                 605

Leu Lys Asp Glu Lys Asn Glu Asn Tyr Ile Tyr Glu Asp Thr Asn Asn
    610                 615                 620

Asn Leu Glu Asp Tyr Gln Thr Ile Thr Lys Arg Phe Thr Thr Gly Thr
625                 630                 635                 640

Asp Ser Thr Gly Val Tyr Leu Ile Phe Asn Ser Gln Asn Gly Asp Glu
                645                 650                 655

Ala Trp Gly Asp Asn Phe Ile Ile Leu Glu Ile Ser Pro Cys Glu Lys
            660                 665                 670

Leu Leu Ser Pro Glu Leu Ile Lys Thr Asp Lys Trp Ile Ser Thr Gly
        675                 680                 685

Ser Thr Tyr Ile Ser Asp Asp Arg Leu Thr Leu Tyr Gln Gly Gly Arg
    690                 695                 700

Gly Ile Leu Lys Gln Asn Leu Gln Leu Asp Arg Phe Ser Thr Tyr Arg
705                 710                 715                 720
```

-continued

```
Val Asn Phe Ser Val Asn Gly Asp Ala Asn Val Arg Ile Arg Asn Ser
                725                 730                 735

Arg Glu Val Leu Leu Glu Lys Arg Tyr Leu Asn Arg Lys Gly Val Ser
            740                 745                 750

Glu Met Phe Thr Thr Lys Phe Asp Lys Asp Asn Phe Tyr Val Glu Leu
        755                 760                 765

Ser Gln Gly Asp Asn Leu Gly Thr Val Val His Phe Tyr Asp Phe Ser
    770                 775                 780

Ile Lys
785


<210> SEQ ID NO 20
<211> LENGTH: 17
<212> TYPE: DNA
<213> ORGANISM: Artificial Sequence
<220> FEATURE:
<223> OTHER INFORMATION: SUP-1A forward primer

<400> SEQUENCE: 20

ggattcgtta tcagaaa                                                   17


<210> SEQ ID NO 21
<211> LENGTH: 17
<212> TYPE: DNA
<213> ORGANISM: Artificial Sequence
<220> FEATURE:
<223> OTHER INFORMATION: SUP-1B reverse primer

<400> SEQUENCE: 21

ctgtygctaa caatgtc                                                   17


<210> SEQ ID NO 22
<211> LENGTH: 47
<212> TYPE: DNA
<213> ORGANISM: Artificial Sequence
<220> FEATURE:
<223> OTHER INFORMATION: SUP primer

<400> SEQUENCE: 22

gctctagaag gaggtaactt atgaacaaga ataatactaa attaagc                  47


<210> SEQ ID NO 23
<211> LENGTH: 27
<212> TYPE: DNA
<213> ORGANISM: Artificial Sequence
<220> FEATURE:
<223> OTHER INFORMATION: SUP primer

<400> SEQUENCE: 23

ggggtacctt acttaataga gacatcg                                        27


<210> SEQ ID NO 24
<211> LENGTH: 2364
<212> TYPE: DNA
<213> ORGANISM: Bacillus thuringiensis

<400> SEQUENCE: 24

atgaatatga ataatactaa attaaacgca agggccctac cgagttttat tgattatttt     60

aatggcattt atggatttgc cactggtatc aaagacatta tgaatatgat ttttaaaacg    120

gatacaggtg gtaatctaac cttagacgaa atcctaaaga atcagcagtt actaaatgag    180

atttctggta aattggatgg ggtaaatggg agcttaaatg atcttatcgc acagggaaac    240
```

-continued ttaaatacag aattatctaa ggaaatctta aaaattgcaa atgaacagaa tcaagtctta 300
aatgatgtta ataacaaact cgatgcgata aatacgatgc ttcatatata tctacctaaa 360
atcacatcta tgttaagtga tgtaatgaag caaaattatg cgctaagtct gcaagtagaa 420
tacttaagta aacaattgaa agaaatttct gataaattag atgttattaa cgtaaatgtt 480
cttattaact ctacacttac tgaaattaca cctgcatatc aacggattaa atatgtaaat 540
gaaaaatttg aagaattaac ttttgctaca gaaaccactt taaaagtaaa aaaggatagc 600
tcgcctgctg atattcttga cgagttaact gaattaactg aactagcgaa aagtgttaca 660
aaaaatgacg tggatggttt tgaattttac cttaatacat tccacgatgt aatggtagga 720
aataatttat tcgggcgttc agctttaaaa actgcttcag aattaattgc taaagaaaat 780
gtgaaaacaa gtggcagtga agtaggaaat gtttataatt tcttaattgt attaacagct 840
ctacaagcaa aagcttttct tactttaaca acatgccgaa aattattagg cttagcagat 900
attgattata catctattat gaatgaacat ttaaataagg aaaaagagga atttagagta 960
aacatccttc ctacactttc taatactttt tctaatccta attatgcaaa agttaaagga 1020
agtgatgaag atgcaaagat gattgtggaa gctaaaccag gacatgcatt ggttgggttt 1080
gaaattagta atgattcaat gacagtatta aaagtatatg aagctaagct aaaacaaaat 1140
taccaagttg ataaggattc cttatcggaa gtcatttata gtgatatgga taaattattg 1200
tgcccagatc aatctgaaca aatttattat acaaataata tagtatttcc aaatgaatat 1260
gtaattacta aaattgattt tactaagaaa atgaaaactt taagatatga ggtaacagct 1320
aattcttacg attcttctac aggagaaatt gacttaaata agaagaaagt agaatcaagt 1380
gaagcggagt ataggacgtt aagtgctaat aatgatggag tatatatgcc gttaggtgtc 1440
atcagtgaaa catttttgac tccaattaat ggatttggcc tccaagctga tgaaaattca 1500
agattaatta ctttaacatg taaatcatat ttaagggaac tactactagc gacagactta 1560
agcaataaag aaactaaatt gattgtcccg cctattagtt ttattagtaa tattgtagaa 1620
aatgggaact tagagggaga aaacttagag ccgtggatag caaataacaa aaatgcgtat 1680
gtagatcata caggtggtat aaatggaact aaagttttat atgttcataa ggatggtgag 1740
ttttcacaat ttgttggagg taagttaaaa tcgaaaacag aatatgtaat tcaatatatt 1800
gtaaagggaa aagcttctat ttatttaaaa gataaaaaaa atgagaattc catttatgaa 1860
gaaataaata atgatttaga aggttttcaa actgttacta aacgttttat tacaggaacg 1920
gattcttcag ggattcattt aatttttacc agtcaaaatg gcgagggagc atttggagga 1980
aactttatta tctcagaaat taggacatcc gaagagttat taagtccaga attgattatg 2040
tcggatgctt gggttggatc ccagggaact tggatctcag gaaattctct cactattaat 2100
agtaatgtaa atggaacctt tcgacaaaat cttccgttag aaagttattc aacctatagt 2160
atgaacttta ctgtgaatgg atttggcaag gtgacagtaa gaaattctcg tgaagtatta 2220
tttgaaaaaa gttatccgca gctttcacct aaagatattt ctgaaaaatt tacaactgca 2280
gccaataata ccggattata tgtagagctt tctcgctcaa cgtcgggtgg tgcaataaat 2340
ttccgagatt tttcaattaa gtaa 2364

<210> SEQ ID NO 25
<211> LENGTH: 787
<212> TYPE: PRT
<213> ORGANISM: Bacillus thuringiensis -continued

<400> SEQUENCE: 25

```
Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Val Glu Tyr Leu Ser Lys
    130                 135                 140

Gln Leu Lys Glu Ile Ser Asp Lys Leu Asp Val Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Ile Ser Asn Asp Ser Met Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Ser Asp Met Asp Lys Leu Leu
385                 390                 395                 400

Cys Pro Asp Gln Ser Glu Gln Ile Tyr Tyr Thr Asn Asn Ile Val Phe
                405                 410                 415
```

-continued

```
Pro Asn Glu Tyr Val Ile Thr Lys Ile Asp Phe Thr Lys Lys Met Lys
            420                 425                 430

Thr Leu Arg Tyr Glu Val Thr Ala Asn Ser Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asn Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ile Ser Phe Ile Ser Asn Ile Val Glu Asn Gly Asn Leu
    530                 535                 540

Glu Gly Glu Asn Leu Glu Pro Trp Ile Ala Asn Asn Lys Asn Ala Tyr
545                 550                 555                 560

Val Asp His Thr Gly Gly Ile Asn Gly Thr Lys Val Leu Tyr Val His
                565                 570                 575

Lys Asp Gly Glu Phe Ser Gln Phe Val Gly Gly Lys Leu Lys Ser Lys
            580                 585                 590

Thr Glu Tyr Val Ile Gln Tyr Ile Val Lys Gly Lys Ala Ser Ile Tyr
        595                 600                 605

Leu Lys Asp Lys Lys Asn Glu Asn Ser Ile Tyr Glu Glu Ile Asn Asn
    610                 615                 620

Asp Leu Glu Gly Phe Gln Thr Val Thr Lys Arg Phe Ile Thr Gly Thr
625                 630                 635                 640

Asp Ser Ser Gly Ile His Leu Ile Phe Thr Ser Gln Asn Gly Glu Gly
                645                 650                 655

Ala Phe Gly Gly Asn Phe Ile Ile Ser Glu Ile Arg Thr Ser Glu Glu
            660                 665                 670

Leu Leu Ser Pro Glu Leu Ile Met Ser Asp Ala Trp Val Gly Ser Gln
        675                 680                 685

Gly Thr Trp Ile Ser Gly Asn Ser Leu Thr Ile Asn Ser Asn Val Asn
    690                 695                 700

Gly Thr Phe Arg Gln Asn Leu Pro Leu Glu Ser Tyr Ser Thr Tyr Ser
705                 710                 715                 720

Met Asn Phe Thr Val Asn Gly Phe Gly Lys Val Thr Val Arg Asn Ser
                725                 730                 735

Arg Glu Val Leu Phe Glu Lys Ser Tyr Pro Gln Leu Ser Pro Lys Asp
            740                 745                 750

Ile Ser Glu Lys Phe Thr Thr Ala Ala Asn Asn Thr Gly Leu Tyr Val
        755                 760                 765

Glu Leu Ser Arg Ser Thr Ser Gly Gly Ala Ile Asn Phe Arg Asp Phe
    770                 775                 780

Ser Ile Lys
785
```

<210> SEQ ID NO 26
<211> LENGTH: 2367
<212> TYPE: DNA
<213> ORGANISM: Bacillus thuringiensis -continued

<400> SEQUENCE: 26

```
atggctaaca tgaacaacac caagctcaac gcccgcgccc tcccatcctt cattgactac     60
ttcaacggca tctacggctt cgccactggc atcaaggaca tcatgaacat gatcttcaag    120
actgacactg gtggcaacct caccttggat gagatcctca agaaccagca gctcctcaac    180
gagatctctg gcaagttgga tggtgtcaac ggctccctca acgacctcat tgcccagggc    240
aacctcaaca ctgagctttc caaggagatc ctcaaaattg ccaacgagca gaaccaggtc    300
ctcaacgatg tcaacaacaa gttggatgcc atcaacacca tgctccacat ctatctccca    360
aaaatcacct ccatgctctc tgatgtcatg aagcagaact acgccctctc cctccaagtg    420
gagtacctct ccaagcagct caaggaaatt tctgacaagt tggatgtgat caacgtcaac    480
gtcctcatca actccaccct cactgagatc actccagcct atcagaggat caagtacgtc    540
aacgagaagt tcgaggagct tactttcgcc actgagacca ccctcaaggt caagaaggac    600
tccagcccag ctgacatctt ggatgagctt actgagctta ctgagttggc caagtctgtc    660
accaagaacg atgtggatgg cttcgagttc tacctcaaca ccttccacga tgtcatggtg    720
ggcaacaact tgttcggccg ttctgccctc aagactgcct ctgaattgat cgcaaaggag    780
aacgtcaaga cctctggctc tgaggtgggc aacgtctaca acttcctcat tgtcctcact    840
gccctccaag ccaaggcctt cctcaccctc accacctgtc gtaagctctt gggcttggct    900
gacattgact acacctccat catgaacgag cacctcaaca aggagaagga ggagttccgt    960
gtcaacatcc tcccaaccct ctccaacacc ttctccaacc caaactacgc caaggtcaag   1020
ggctctgatg aggatgccaa gatgattgtg gaggccaagc ccggccacgc ccttgtgggc   1080
ttcgagatct ccaacgactc catgactgtc ctcaaggtct acgaggccaa gctcaagcag   1140
aactaccagg tggacaagga ctccctctcc gaggtcatct actccgacat ggacaagctc   1200
ctctgcccag accagtccga gcagatctac tacaccaaca acatcgtgtt cccaaacgag   1260
tacgtcatca ccaaaattga cttcaccaag aagatgaaaa ccctccgtta cgaggtcact   1320
gccaactcct acgactcctc cactggtgag attgacctca acaagaagaa ggtggagtcc   1380
tctgaggctg agtaccgtac cctctctgcc aacaacgatg gtgtctacat gcccttgggt   1440
gtgatctctg agaccttcct cactcctatc aacggtttcg gcctccaagc tgatgaaaat   1500
tcacgtctca tcaccctcac ttgtaagtcc tatctcaggg agttgctctt ggccactgac   1560
ctctccaaca aggagaccaa gctcattgtc ccacccatct ccttcatctc caacattgtg   1620
gagaacggca acttggaggg tgagaacttg gagccttgga ttgccaacaa caagaacgcc   1680
tacgtggacc acactggtgg catcaacggc accaaggtcc tctacgtcca caaggatggt   1740
gagttctccc agttcgtggg tggcaagttg aagtccaaga ctgagtacgt catccagtac   1800
attgtcaagg gcaaggcctc catctatctc aaggacaaga aaaatgagaa ctccatctac   1860
gaggagatca acaacgactt ggagggcttc cagactgtca ccaagaggtt catcactggc   1920
actgactcct ctggcatcca cctcatcttc acctcccaga acggtgaggg tgctttcggt   1980
ggcaacttca taatctctga gatcaggacc tctgaggagc ttctctctcc cgagcttatc   2040
atgtctgatg cctgggttgg ctcccagggc acttggatct ctggcaactc cctcaccatc   2100
aactccaacg tcaacggcac cttccgccag aacctcccat tggagtccta ctccacctac   2160
tccatgaact tcactgtcaa cggtttcggc aaggtcactg tcaggaactc ccgtgaggtc   2220
ctcttcgaga agtcctaccc acagctctct cccaaggaca tctctgagaa gttcaccact   2280
```

-continued gctgccaaca acactggcct ctacgtggag ctttcccgtt ccacctctgg tggtgccatc 2340
aacttccgtg acttctccat caagtga 2367

<210> SEQ ID NO 27
<211> LENGTH: 788
<212> TYPE: PRT
<213> ORGANISM: Bacillus thuringiensis

<400> SEQUENCE: 27

Met Ala Asn Met Asn Asn Thr Lys Leu Asn Ala Arg Ala Leu Pro Ser
1 5 10 15

Phe Ile Asp Tyr Phe Asn Gly Ile Tyr Gly Phe Ala Thr Gly Ile Lys
20 25 30

Asp Ile Met Asn Met Ile Phe Lys Thr Asp Thr Gly Gly Asn Leu Thr
35 40 45

Leu Asp Glu Ile Leu Lys Asn Gln Gln Leu Leu Asn Glu Ile Ser Gly
50 55 60

Lys Leu Asp Gly Val Asn Gly Ser Leu Asn Asp Leu Ile Ala Gln Gly
65 70 75 80

Asn Leu Asn Thr Glu Leu Ser Lys Glu Ile Leu Lys Ile Ala Asn Glu
85 90 95

Gln Asn Gln Val Leu Asn Asp Val Asn Asn Lys Leu Asp Ala Ile Asn
100 105 110

Thr Met Leu His Ile Tyr Leu Pro Lys Ile Thr Ser Met Leu Ser Asp
115 120 125

Val Met Lys Gln Asn Tyr Ala Leu Ser Leu Gln Val Glu Tyr Leu Ser
130 135 140

Lys Gln Leu Lys Glu Ile Ser Asp Lys Leu Asp Val Ile Asn Val Asn
145 150 155 160

Val Leu Ile Asn Ser Thr Leu Thr Glu Ile Thr Pro Ala Tyr Gln Arg
165 170 175

Ile Lys Tyr Val Asn Glu Lys Phe Glu Glu Leu Thr Phe Ala Thr Glu
180 185 190

Thr Thr Leu Lys Val Lys Lys Asp Ser Ser Pro Ala Asp Ile Leu Asp
195 200 205

Glu Leu Thr Glu Leu Thr Glu Leu Ala Lys Ser Val Thr Lys Asn Asp
210 215 220

Val Asp Gly Phe Glu Phe Tyr Leu Asn Thr Phe His Asp Val Met Val
225 230 235 240

Gly Asn Asn Leu Phe Gly Arg Ser Ala Leu Lys Thr Ala Ser Glu Leu
245 250 255

Ile Ala Lys Glu Asn Val Lys Thr Ser Gly Ser Glu Val Gly Asn Val
260 265 270

Tyr Asn Phe Leu Ile Val Leu Thr Ala Leu Gln Ala Lys Ala Phe Leu
275 280 285

Thr Leu Thr Thr Cys Arg Lys Leu Leu Gly Leu Ala Asp Ile Asp Tyr
290 295 300

Thr Ser Ile Met Asn Glu His Leu Asn Lys Glu Lys Glu Glu Phe Arg
305 310 315 320

Val Asn Ile Leu Pro Thr Leu Ser Asn Thr Phe Ser Asn Pro Asn Tyr
325 330 335

Ala Lys Val Lys Gly Ser Asp Glu Asp Ala Lys Met Ile Val Glu Ala
340 345 350

-continued

```
Lys Pro Gly His Ala Leu Val Gly Phe Glu Ile Ser Asn Asp Ser Met
        355                 360                 365

Thr Val Leu Lys Val Tyr Glu Ala Lys Leu Lys Gln Asn Tyr Gln Val
    370                 375                 380

Asp Lys Asp Ser Leu Ser Glu Val Ile Tyr Ser Asp Met Asp Lys Leu
385                 390                 395                 400

Leu Cys Pro Asp Gln Ser Glu Gln Ile Tyr Tyr Thr Asn Asn Ile Val
                405                 410                 415

Phe Pro Asn Glu Tyr Val Ile Thr Lys Ile Asp Phe Thr Lys Lys Met
            420                 425                 430

Lys Thr Leu Arg Tyr Glu Val Thr Ala Asn Ser Tyr Asp Ser Ser Thr
        435                 440                 445

Gly Glu Ile Asp Leu Asn Lys Lys Lys Val Glu Ser Ser Glu Ala Glu
    450                 455                 460

Tyr Arg Thr Leu Ser Ala Asn Asn Asp Gly Val Tyr Met Pro Leu Gly
465                 470                 475                 480

Val Ile Ser Glu Thr Phe Leu Thr Pro Ile Asn Gly Phe Gly Leu Gln
                485                 490                 495

Ala Asp Glu Asn Ser Arg Leu Ile Thr Leu Thr Cys Lys Ser Tyr Leu
            500                 505                 510

Arg Glu Leu Leu Leu Ala Thr Asp Leu Ser Asn Lys Glu Thr Lys Leu
        515                 520                 525

Ile Val Pro Pro Ile Ser Phe Ile Ser Asn Ile Val Glu Asn Gly Asn
    530                 535                 540

Leu Glu Gly Glu Asn Leu Glu Pro Trp Ile Ala Asn Asn Lys Asn Ala
545                 550                 555                 560

Tyr Val Asp His Thr Gly Gly Ile Asn Gly Thr Lys Val Leu Tyr Val
                565                 570                 575

His Lys Asp Gly Glu Phe Ser Gln Phe Val Gly Gly Lys Leu Lys Ser
            580                 585                 590

Lys Thr Glu Tyr Val Ile Gln Tyr Ile Val Lys Gly Lys Ala Ser Ile
        595                 600                 605

Tyr Leu Lys Asp Lys Lys Asn Glu Asn Ser Ile Tyr Glu Glu Ile Asn
    610                 615                 620

Asn Asp Leu Glu Gly Phe Gln Thr Val Thr Lys Arg Phe Ile Thr Gly
625                 630                 635                 640

Thr Asp Ser Ser Gly Ile His Leu Ile Phe Thr Ser Gln Asn Gly Glu
                645                 650                 655

Gly Ala Phe Gly Gly Asn Phe Ile Ile Ser Glu Ile Arg Thr Ser Glu
            660                 665                 670

Glu Leu Leu Ser Pro Glu Leu Ile Met Ser Asp Ala Trp Val Gly Ser
        675                 680                 685

Gln Gly Thr Trp Ile Ser Gly Asn Ser Leu Thr Ile Asn Ser Asn Val
    690                 695                 700

Asn Gly Thr Phe Arg Gln Asn Leu Pro Leu Glu Ser Tyr Ser Thr Tyr
705                 710                 715                 720

Ser Met Asn Phe Thr Val Asn Gly Phe Gly Lys Val Thr Val Arg Asn
                725                 730                 735

Ser Arg Glu Val Leu Phe Glu Lys Ser Tyr Pro Gln Leu Ser Pro Lys
            740                 745                 750

Asp Ile Ser Glu Lys Phe Thr Thr Ala Ala Asn Asn Thr Gly Leu Tyr
        755                 760                 765
```

-continued

```
Val Glu Leu Ser Arg Ser Thr Ser Gly Gly Ala Ile Asn Phe Arg Asp
    770                 775                 780

Phe Ser Ile Lys
785
```